(12) United States Patent
Guan et al.

(10) Patent No.: US 12,282,023 B2
(45) Date of Patent: Apr. 22, 2025

(54) USE OF ZC3H12B GENE OR PROTEIN AND METHOD FOR ESTABLISHING ANIMAL MODEL OF LIVER DISEASE

(71) Applicant: SHANGHAI OCEAN UNIVERSITY, Shanghai (CN)

(72) Inventors: Guijun Guan, Shanghai (CN); Yuyang Chang, Shanghai (CN)

(73) Assignee: SHANGHAI OCEAN UNIVERSITY, Shanghai (CN)

( * ) Notice: Subject to any disclaimer, the term of this patent is extended or adjusted under 35 U.S.C. 154(b) by 1068 days.

(21) Appl. No.: 17/135,890

(22) Filed: Dec. 28, 2020

(65) Prior Publication Data
US 2021/0199661 A1    Jul. 1, 2021

Related U.S. Application Data

(63) Continuation of application No. PCT/CN2020/072609, filed on Jan. 17, 2020.

(51) Int. Cl.
*G01N 33/574* (2006.01)
*A01K 67/0275* (2024.01)
*G01N 33/68* (2006.01)

(52) U.S. Cl.
CPC ... *G01N 33/57484* (2013.01); *A01K 67/0275* (2013.01); *G01N 33/57438* (2013.01); *G01N 33/6893* (2013.01); *A01K 2217/075* (2013.01); *G01N 2333/705* (2013.01); *G01N 2400/40* (2013.01)

(58) Field of Classification Search
CPC ....... G01N 33/57484; G01N 33/57438; G01N 33/6893; G01N 2333/705; G01N 2400/40; G01N 2333/922; A01K 67/0275; A01K 2217/075; A01K 2227/40; A01K 2267/035; C07K 14/4705; C12N 9/16; C12Y 301/00; C12Q 2600/158; C12Q 1/6883
USPC ...................................... 800/8, 10
See application file for complete search history.

(56) References Cited

PUBLICATIONS

Wawro et al., "ZC3H12B/MCPIP2, a new active member of the ZC3H12 family". RNA. Jul. 2019;25(7):840-856. doi: 10.1261/rna. 071381.119. Epub Apr. 15, 2019. (Year: 2019).*
Miao et al., "Targeted disruption of MCPIP1/Zc3h12a results in fatal inflammatory disease". Immunol Cell Biol. May 2013;91(5):368-76. doi: 10.1038/icb.2013.11. Epub Apr. 9, 2013. (Year: 2013).*

* cited by examiner

*Primary Examiner* — Allison M Fox
*Assistant Examiner* — Hanan Isam Abuzeineh

(57) ABSTRACT

The gene editing technology was used to carry out target knockout of zc3h12b gene of *Oryzias latipes*, establishing *Oryzias latipes* missing Zc3h12b protein product. The established *Oryzias latipes* all show different degrees of liver lesions such as hepatobiliary duct hyperplasia and fusion, hepatocyte steatosis, and fibrosis. With increase of months, significant fatty liver appears with local cyst necrosis, obvious lymphocyte infiltration in liver sinusoids and abnormal increase in number of macrophages. Human tumor markers cytokeratin 19 (CK19), smooth muscle actin (SMA) and glypican-3 (GPC3) positive cells are also detected. It is suggested that ZC3H12B can be used as a treatment target and a biomarker for biliary cystadenoma (BCA), biliary cystadenocarcinoma (BCAC), or fatty liver or liver cancer related to BCA or BCAC. The zc3h12b missing *Oryzias latipes* can be used as an animal model in researches on pathological processes of BCA, BCAC, or fatty liver or liver cancer related to BCA or BCAC.

2 Claims, 11 Drawing Sheets
Specification includes a Sequence Listing.

FIG. 2

USE OF ZC3H12B GENE OR PROTEIN AND METHOD FOR ESTABLISHING ANIMAL MODEL OF LIVER DISEASE

CROSS-REFERENCE TO RELATED APPLICATIONS

This application is a continuation of International Patent Application No. PCT/CN2020/072609 with a filing date of Jan. 17, 2020, designating the United States, now pending, and further claims priority to Chinese Patent Application No. 201911399060.4 with a filing date of Dec. 30, 2019. The content of the aforementioned applications, including any intervening amendments thereto, are incorporated herein by reference.

CROSS-REFERENCE TO A SEQUENCE LISTING

This application includes a Sequence Listing submitted electronically as a text file named US_SL_ST25.txt, created on Jan. 7, 2020, with a size of 30,587 bytes. The Sequence Listing is incorporated by reference herein.

TECHNICAL FIELD

The present disclosure relates to the field of biomedical technology, in particular to new functions of gene or protein and establishment of animal models of related diseases. Specifically, the present disclosure relates to the use of ZC3H12B gene or protein and a method for establishing an animal model capable of simulating liver disease.

BACKGROUND

Liver diseases can be divided into non-neoplastic and neoplastic liver diseases. The non-neoplastic liver diseases include common pathogenic infections such as hepatitis viruses or parasites, chemical or alcoholic liver damage, and genetic developmental abnormalities such as cholelithiasis and bile duct malformations. For the non-neoplastic liver diseases, the microenvironment where hepatocytes, bile duct epithelial cells and stem cells in liver sinusoids are present is constantly stimulated by bile secreted by bile duct epithelium. The microenvironment is also affected by cytokines secreted by natural macrophages (Kupffer cell, KC) of the liver sinusoids and lymphocytes which regulate the autoimmune system. This leads to hepatocellular fatty lesions, fibrosis, then liver cirrhosis, and even liver tumor carcinogenesis at a local damage site of the liver. Epidemiological survey data show that, men and woman have different incidence rates of hepatocellular carcinoma (HCC) and intrahepatic cholangiocarcinoma (ICC). A ratio of HCC incidence is about 2:1-4:1 between men and women, while women have a higher incidence rate of ICC than men (3:2). ICC is a bile duct adenocarcinoma originating from hepatic bile duct epithelial cells, hepatocytes, stem cells, and parabiliary gland cells. Its incidence is second only to liver primary malignant tumor of HCC. Pathogenic factors of ICC include inflammation of the bile duct caused by pathogenic infections such as hepatitis virus and parasites, chemical carcinogens, and genetic factors. However, its pathogenic mechanism and exact cause are still unknown, and incidence of ICC has shown an upward trend in recent years. Since the ICC has no obvious clinical symptoms at an early stage, early diagnosis and timely treatment are of great special significance. Current researches explain sexual differences in ICC liver cancer mainly based on sex hormones and cytokines. However, in recent years, treatment protocols based on estrogen and androgen receptor pathways and inflammatory intervention have not achieved expected therapeutic results in clinical practice. One reason is that, many existing research results are obtained from chemically induced animal models of liver cancer which cannot fully simulate clinical ICC caused by hepatitis B virus (HBV) and hepatitis C virus (HCV) infections, especially the process of ICC caused by genetic factors. Another reason is that, since there are different types of cells involved in ICC, reasons and mechanisms of sexual differences are not completely clear, and ICC animal models are established by drugs, there is a lack of in-depth research at genome level. Therefore, ICC animal models based on gene and protein molecules are important for basic science and clinical practice, for example, researches on pathogenic mechanism of liver cancer and sexual difference at a molecular gene level, development of rapid diagnostic technology, and design and screening of targeting drugs.

Zc3h12 protein family is a class of CCCH-type zinc finger proteins act on immune and inflammatory responses. It is characterized by a CCCH-type zinc finger domain (related to DNA or RNA binding), a PIN Zc3h12 functional domain, and an RNase active region, as well as an independent ubiquitin-related functional domain (UBA) that is highly conserved in the ZC3H12 family (FIGS. 2-3). The Zc3h12 protein family includes 4 members: ZC3H12A, ZC3H12B, ZC3H12C and ZC3H12D. Although these four proteins are highly homologous in amino acid sequence, they are very different in tissue distribution. Functions of the Zc3h12 protein family are not fully understood yet. For Zc3h12b, Wawro M. et al. (Wawro M., Wawro K., Kochan J., Solecka A., Sowinska W., Lichawska-Cieslar A., et al., Zc3h12b/ MCPIP2, a new active member of the ZC3H12 family; RNA. 25 (2019) 840-856) discloses a human and mammalian ZC3H12B, which has functions of binding proinflammatory interleukin-6 (IL-6) mRNA, and is present in cytoplasm to form particles (granule-like structure), regulating mRNA transcription and protein translation to stop a cell cycle at G2 phase. However, as of the filing date of this disclosure, there has been no report on relationship between Zc3h12b and liver diseases especially ICC and its related fatty liver and liver cancer, and no report of animal models of liver diseases obtained by knocking out Zc3h12b in mice or any other animals.

SUMMARY

In view of deficiencies in the prior art, an objective of the present disclosure is to provide use of ZC3H12B gene or protein, and based on this, provide a method for establishing an animal model of liver disease.

A first aspect of the present disclosure provides use of ZC3H12B gene or protein or an up-regulator thereof in preparing a pharmaceutical for treating biliary cystadenoma (BCA), biliary cystadenocarcinoma (BCAC), or fatty liver or liver cancer related to BCA or BCAC.

As a preferred embodiment of the present disclosure, the up-regulator may be selected from the group consisting of small molecule compounds and biological macromolecules.

A second aspect of the present disclosure provides a pharmaceutical composition for treating BCA, BCAC, or fatty liver or liver cancer related to BCA or BCAC, including an up-regulator of ZC3H12B gene or protein and a pharmaceutically acceptable carrier.

A third aspect of the present disclosure provides use of ZC3H12B gene or protein as a diagnostic marker in preparing a diagnostic reagent or kit for BCA, BCAC, or fatty liver or liver cancer related to BCA or BCAC.

A fourth aspect of the present disclosure provides a reagent for detecting ZC3H12B gene or protein content in preparing a diagnostic reagent or kit for BCA, BCAC, or fatty liver or liver cancer related to BCA or BCAC.

A fifth aspect of the present disclosure provides a method for screening a pharmaceutical for treating BCA, BCAC, or fatty liver or liver cancer related to BCA or BCAC with ZC3H12B gene or protein as a target, including:

Treating a system expressing ZC3H12B gene or protein with a candidate substance; and Detecting expression of ZC3H12B gene or protein in the system; where, If the expression of ZC3H12B gene or protein is upregulated by the candidate substance, the candidate substance is a desired potential substance; otherwise, the candidate substance is not a desired potential substance.

A sixth aspect of the present disclosure provides a method for establishing an animal model of liver disease, including a step of knocking down expression of Zc3h12b gene or protein of an animal.

As a preferred embodiment of the present disclosure, the liver disease may be selected from BCA, BCAC, or fatty liver or liver cancer related to BCA or BCAC.

As another preferred embodiment of the present disclosure, the animal may be selected from lower to higher vertebrates other than human.

A seventh aspect of the present disclosure provides use of an animal model of liver disease established according to any one of the above methods, where the use is selected from:

a) use in researches on molecular mechanisms related to occurrence of zc3h12b regulated macrophage mediated fatty liver and liver cancer-like changes in human and/or animal;

b) use in researches on molecular mechanisms of pathogenesis of human or animal BCA, BCAC, or fatty liver or liver cancer related to BCA or BCAC;

c) use in researches on pathogenic mechanisms of liver parenchymal collapse and necrosis and fibrotic carcinogenesis in BCA or BCAC;

d) use in screening mechanisms that affect liver differentiation and development in male and female humans or animals, and regulation mechanism of BCA or BCAC incidence due to internal sexual differences between male and female or exogenous environmental factors.

Advantages of the present disclosure are as follows:

Gene editing technology is for the first time used in the present disclosure to carry out target knockout of zc3h12b gene of *Oryzias latipes* and establish zc3h12b missing *Oryzias latipes*, producing a series of frameshift mutations, and Zc3h12b protein product missing heterozygotes and homozygotes. These heterozygotes and homozygotes all show different degrees of liver lesions, and with increase of months, local fatty liver, bile duct hyperplasia and fibrosis appear, where 6-month-old *Oryzias latipes* shows significant fatty liver and local cyst necrosis. For the control normal group, liver sinusoids of zc3h12b knockout *Oryzias latipes* have obvious lymphocytic infiltration, an abnormal increase in number of macrophages, hepatobiliary hyperplasia and fusion, and hepatocellular lipopathy. Immunohistochemical reaction detection shows presence of smooth muscle actin (SMA) positive cells, glypican-3 (GPC3), SMA, cytokeratin 19 (CK19) and other human hepatobiliary tumor cell marker positive cells. Results also show a significantly increased number of matrix metalloproteinase-9 (MMP9) positive macrophages, accompanied by symptoms similar to human liver cancer, for example, iron particle deposition. Based on the above contents, the following conclusions can be obtained:

1. zc3h12b missing *Oryzias latipes* can be used as an animal model in researches on BCA, BCAC or their pathological processes, providing a live animal research platform for in-depth study of molecular mechanisms of CCC3H-type zinc finger protein Zc3h12b regulating and activating inflammatory response of macrophages, and inherent lipopolysaccharide metabolism-macrophage immune response in other tissues (for example, gonads and brain) other than the liver. Since "liver cancer" is considered a "fat" disease in traditional Chinese medicine, the zc3h12b knockout *Oryzias latipes* is named "fat *Oryzias latipes*". Compared with a chemically induced animal model of liver cancer in the prior art, the animal model of the present disclosure can better simulate clinical occurrence of BCA or BCAC, and better facilitate in-depth discussion of sexual differences in occurrence of BCA or BCAC at a genetic level, where a single gene knockout method is simple and easy to operate.

2. ZC3H12B gene or protein can be used as a target in treating BCA, BCAC, or fatty liver or liver cancer related to BCA or BCAC.

3. ZC3H12B gene or protein can be used as a diagnostic marker for BCA, BCAC, or fatty liver or liver cancer related to BCA or BCAC.

4. ZC3H12B gene or protein can be used as a target in screening a pharmaceutical for treating BCA, BCAC, or fatty liver or liver cancer related to BCA or BCAC.

BRIEF DESCRIPTION OF DRAWINGS

Figure 2:
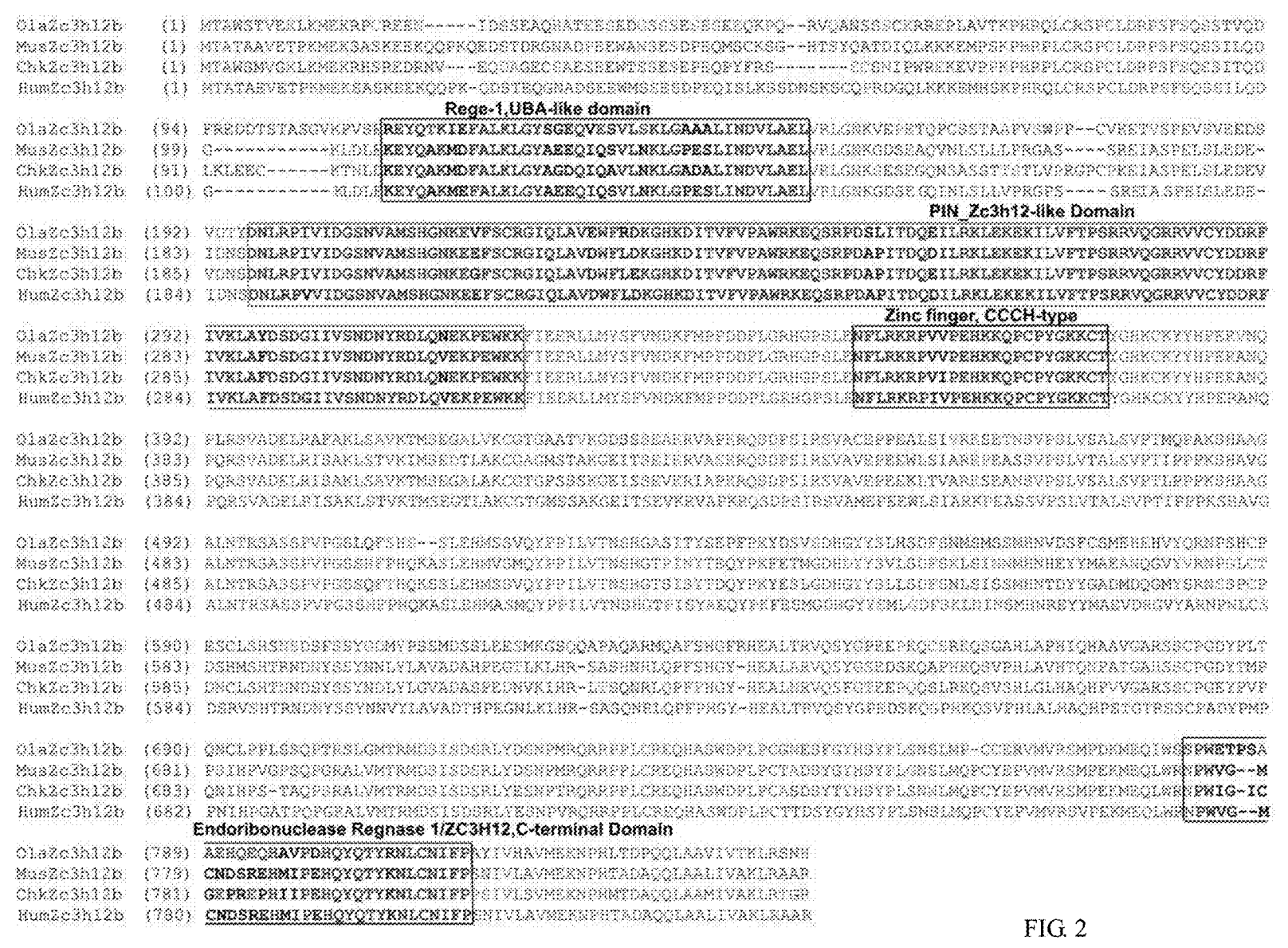

FIGS. 2-3: functional domains in molecular structure of *Oryzias latipes* Zc3h12b protein are highly evolutionarily conserved. FIG. 2: amino acid sequences of Zc3h12b protein of *Oryzias latipes* (SEQ ID NO:11) and those of birds (SEQ ID NO:10) and mammals, mouse (SEQ ID NO:9) and human (SEQ ID NO:8), are highly homologous and conserved in functional domains (green box as a first box: UBA; red box as a second box: PINZc3h12; orange box as a third box: CCCH-type zinc finger domain; blue box as a fourth box: RNase active region). FIG. 3: alignment of multiple sequences is carried out with MUSCLE of the software MEGA X, and an evolutionary tree is drawn with Neighbor-joining tree of MEGA X, concluding that the Zc3h12b protein of *Oryzias latipes* is a Zc3h12 family member. Phylogenetic tree analysis shows four major Zc3h12 family members: Zc3h12A, -B, -C, and -D.

FIG. 4: number and structure of Zc3h12b gene of *Oryzias latipes*, where yellow highlight shows gRNA sequences of two target sites on exon 1 of zc3h12b of *Oryzias latipes*. FIG. 5: Genotype identification of wild type and knockout type by polymerase chain reaction (PCR). FIG. 6: DNA sequencing of wild type and knockout type genomic PCR products for confirmation.

FIG. 7: Antibodies prepared with N-terminal peptides are used to carry out Western blot analysis of Zc3h12b proteins of wild-type and knockout livers. Results show presence of wild-type Zc3h12b (OlaX-201, 845aa, predicted 94.57 kDa; OlaX-202, 833aa, predicted 93.37 kDa) bands, and weakened (Mut3) or no protein expression (Mut1) in knockout livers. This confirms that, after knockout, the Zc3h12b protein is partially or completely destroyed. All the 5 mutants cannot express a complete Zc3h2b protein.

DETAILED DESCRIPTION

Zc3h12b

Figure 1:
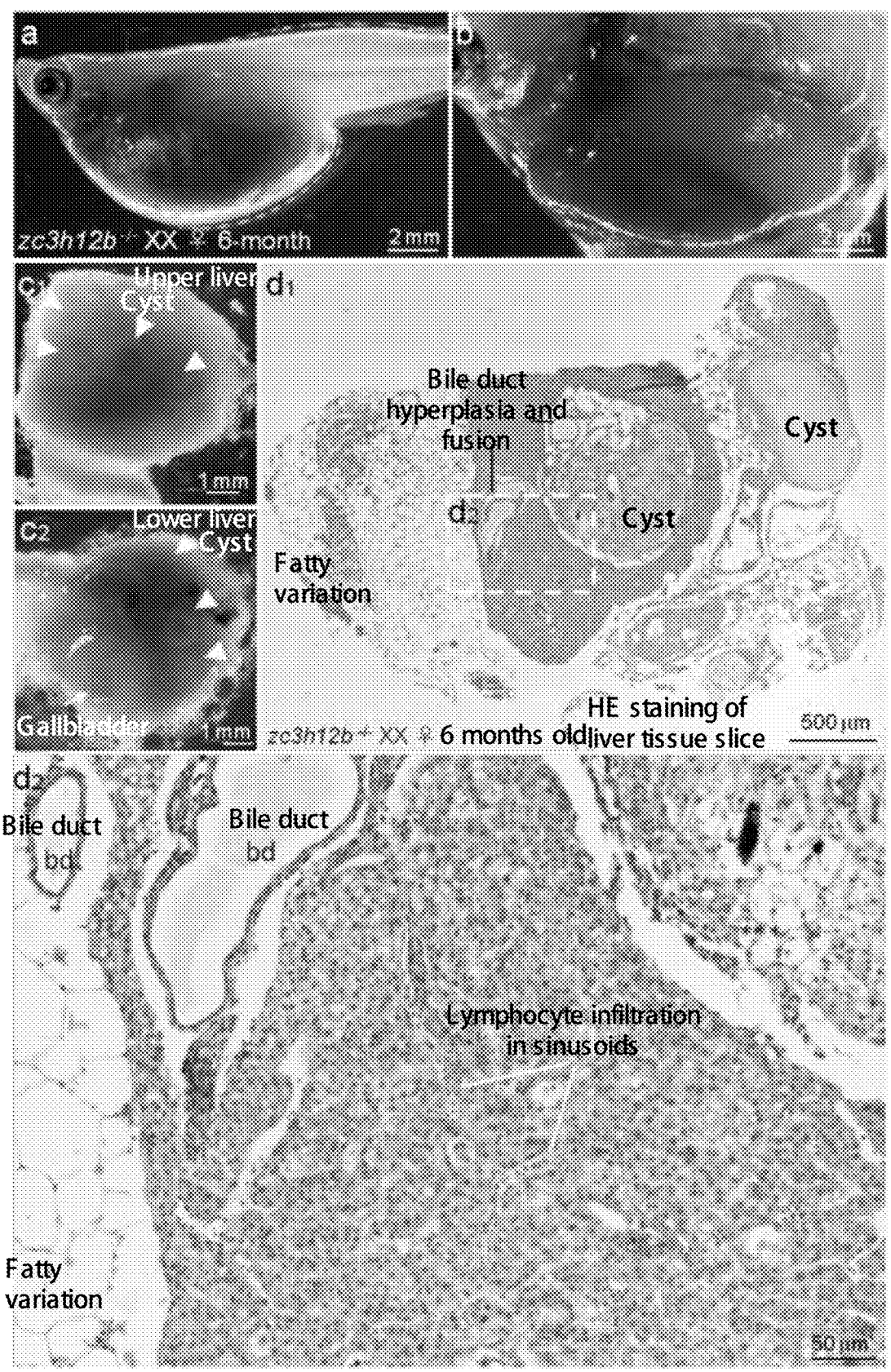
FIG. 1: zc3h12b knockout fat *Oryzias latipes*: hepatobiliary hyperplasia and fusion, ballooning fatty degeneration of hepatocytes (***) and lymphocyte infiltration in liver sinusoid.
Figure 3:
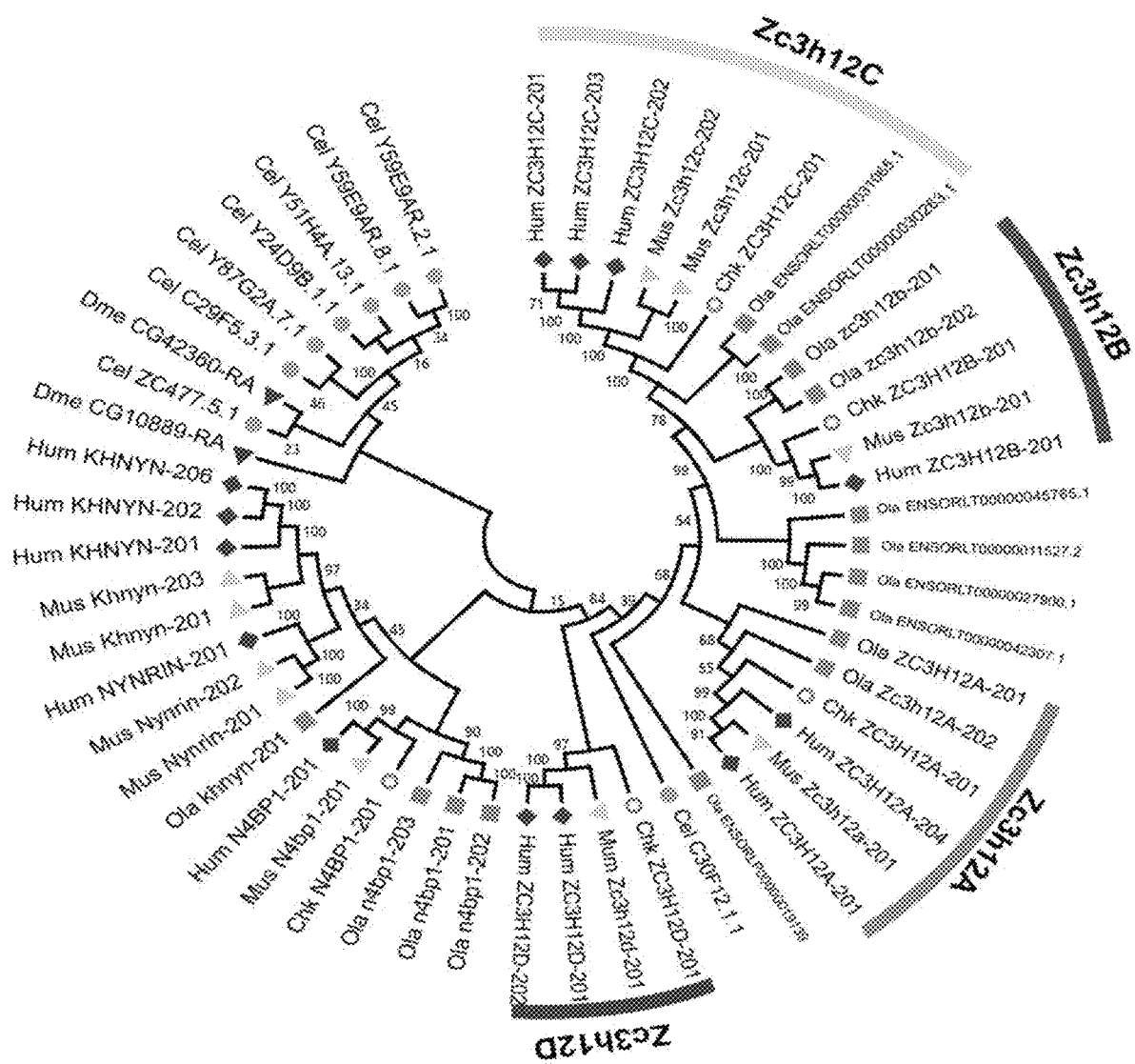
Figure 4:
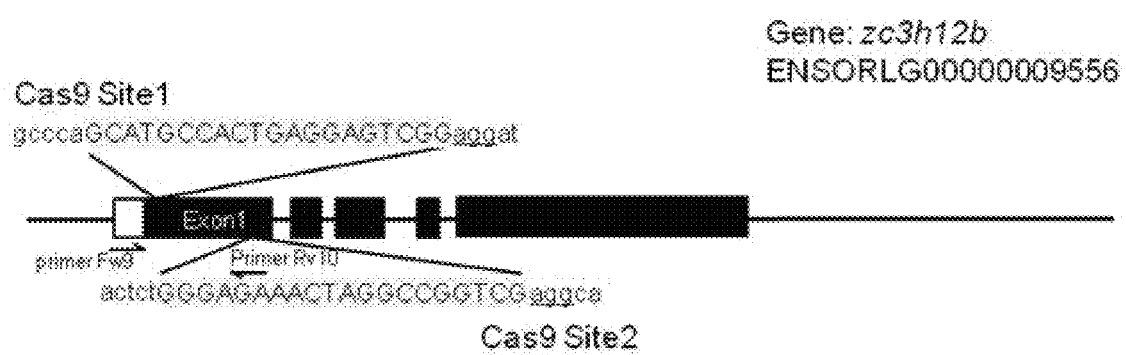
FIGS. 4-7: strategy of target knockout of Zc3h12b gene of *Oryzias latipes* with a CRISPR/CAS9 editing system obtains five *Oryzias latipes* mutants with partial or complete deletion of Zc3h12b.
Figure 5:
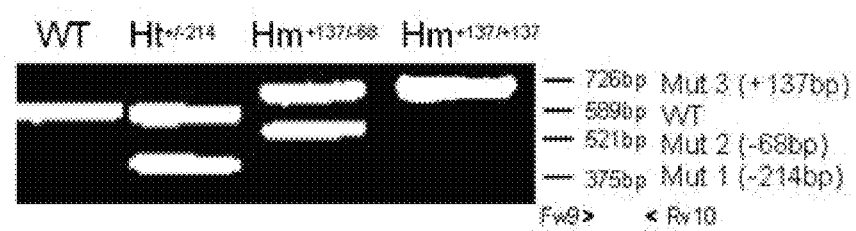
Figure 6:
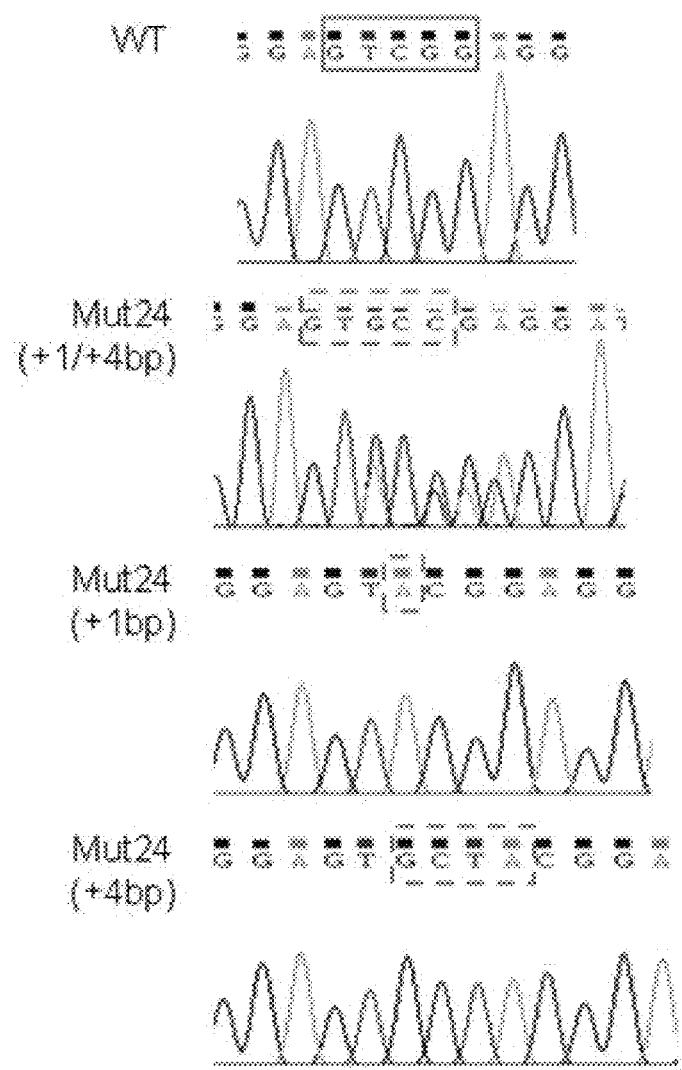
Figure 7:
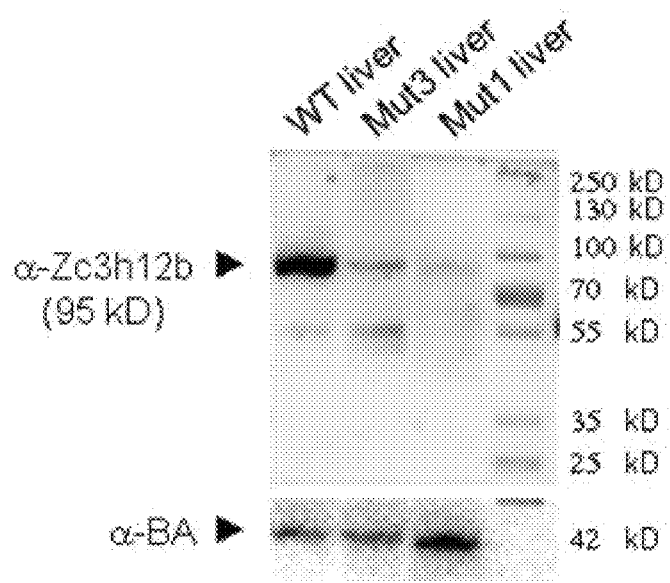

Zc3h12b is one of the members of the Zc3h12 protein family which includes a class of CCCH-type zinc finger proteins acting on immune response and inflammation.

In the present disclosure, the Zc3h12b protein used may be naturally occurring, for example, it may be isolated or purified from lower to higher vertebrates. Moreover, the Zc3h12b protein can also be artificially prepared, for example, a recombinant Zc3h12b protein produced by conventional recombination technology in genetic engineering.

Any suitable Zc3h12b protein can be used in the present disclosure. The Zc3h12b protein may include a full-length Zc3h12b protein or a biologically active fragment thereof.

An amino acid sequence of Zc3h12b protein formed after substitution, deletion or addition of one or more amino acid residues may also be included in the present disclosure. The Zc3h12b protein or the biologically active fragment thereof may include some substitution sequences of conservative amino acids, where the substitution sequences of conservative amino acids do not affect an activity of the protein or retain part of its activity. Appropriate substitution of amino acids is a technique well known in the art, which can be easily implemented to ensure an unchanged biological activity of a resulting molecule. For such a technique, those skilled in the art can realize that, generally speaking, changing a single amino acid in a non-necessary region of a polypeptide does not basically change the biological activity. See Watson et al., Molecular Biology of The Gene, Fourth Edition, 1987, The Benjamin/Cummings Pub. Co. P 224.

Any biologically active fragment of Zc3h12b protein can be applied in the present disclosure. Here, the biologically active fragment of Zc3h12b protein means that as a polypeptide, a fragment can still maintain all or part of the functions of the full-length Zc3h12b protein. Preferably, the biologically active fragment may retain at least 50% of the activity of the full-length Zc3h12b protein. Under more preferable conditions, the active fragment can maintain 60%, 70%, 80%, 90%, 95%, 99%, or 100% of the activity of the full-length Zc3h12b protein.

The present disclosure can also use a modified or improved Zc3h12b protein, for example, a Zc3h12b protein modified or improved in order to promote its half-life, effectiveness, metabolism and/or protein effectiveness. The modified or improved Zc3h12b protein may be a conjugate of the Zc3h12b protein, or it may include substituted or artificial amino acids.

In other words, any variation form which does not affect the biological activity of the Zc3h12b protein can be used in the present disclosure.

Similarly, any naturally occurring, isolated, purified, artificially prepared, modified or improved Zc3h12b gene or fragment thereof which is still capable of encoding the Zc3h12b protein can be used in the present disclosure.

Up-Regulator

As used herein, an up-regulator of the Zc3h12b includes a promoter, an agonist and the like. Any substance which can increase the activity of the Zc3h12b protein, maintain stability of the Zc3h12b protein, promote expression or secretion of the Zc3h12b protein, extend the effective acting time of the Zc3h12b protein, or promote the transcription and translation of the Zc3h12b can be used in the present disclosure.

As a preferred embodiment of the present disclosure, the up-regulator of the Zc3h12b protein may include (but not limited to): an expression vector or an expression construct that can express (preferably overexpress) Zc3h12b after transferring into a cell. Generally, the expression vector contains a gene cassette, where the gene cassette includes a gene encoding Zc3h12b and an expression control sequence operatively connected to the gene. The "operatively connected" or "operably connected to" refers to that, certain parts of a linear DNA sequence can regulate or control activities of other parts of the same linear DNA sequence. For example, if a promoter controls transcription of a coding sequence, the promoter is operatively connected to the coding sequence.

Use

The present disclosure provides use of ZC3H12B gene or protein or an up-regulator thereof in preparing a pharmaceutical for treating BCA, BCAC, or fatty liver or liver cancer related to BCA or BCAC.

Cholangiocarcinoma is a malignant liver tumor which can be divided into two categories: primary and secondary diseases. In the present disclosure, the cholangiocarcinoma preferably refers to primary BCAC, a liver malignant tumor originating from hepatobiliary epithelium. Causes thereof may include HBV and HCV infections, aflatoxin, drinking water pollution, alcohol, liver cirrhosis, sex hormones, nitrosamines, microelements, autoimmune liver disease and the like.

The present disclosure also provides use of ZC3H12B gene or protein as a diagnostic marker in preparing a diagnostic reagent or kit for BCA, BCAC, or fatty liver or liver cancer related to BCA or BCAC. According to the present disclosure, a reagent for detecting ZC3H12B gene or protein content can be used to prepare a diagnostic reagent or kit for BCA, BCAC, or fatty liver or liver cancer related to BCA or BCAC.

Expression of the Zc3h12b protein or its coding gene in a sample (specimen) to be tested can be analyzed to determine disease development in a subject, providing an evidence for diagnosis or prognosis of the disease. The sample to be tested or the specimen to be tested may be a tissue or body fluid of a patient.

Various techniques can be used to determine expression of Zc3h12b, and these techniques are all included in the present disclosure. Existing technologies available for nucleic acid detection include (but are not limited to): gene chip, probe hybridization, PCR, Northern Blot and the like. A protein can be detected by means of a mass spectrometer and the like, or by methods such as Western Blot or enzyme linked immunosorbent assay (ELISA).

The present disclosure also provides a method for screening a pharmaceutical for treating BCA, BCAC, or fatty liver or liver cancer related to BCA or BCAC with ZC3H12B gene or protein as a target, including:

Treating a system expressing ZC3H12B gene or protein with a candidate substance; and Detecting expression of ZC3H12B gene or protein in the system; where, If the expression of ZC3H12B gene or protein is upregulated by the candidate substance, the candidate substance is a desired potential substance; otherwise, the candidate substance is not a desired potential substance.

The system expressing Zc3h12b may be a cell (or cell culture) system, and the cell may be a cell expressing Zc3h12b endogenously or recombinantly. The system expressing Zc3h12b can also be a subcellular system, a solution system, a tissue system, an organ system or an animal system (for example, an animal model, preferably a lower or higher vertebrate model such as fish, mice, rabbits, sheep and monkeys) and the like. In a preferred embodiment of the present disclosure, in order to enable easier observation of changes of Zc3h12b expression during the screening, a control group may also be introduced, where the control group may be a system expressing Zc3h12b without adding the candidate substance.

Animal Model

Based on findings of the present disclosure, a method is provided for establishing an animal model of liver disease, including a step of knocking down expression of zc3h12b gene or protein of an animal. The liver disease may be selected from BCA, BCAC, or fatty liver or liver cancer related to BCA or BCAC. The animal may be selected from lower to higher vertebrates except humans, including fish, amphibians, reptiles, birds, and mammals including mice, dogs, rabbits, monkeys, and humans.

The animal model of the present disclosure can be used as an excellent platform for researches on molecular mechanisms of pathogenesis of BCA, BCAC, or fatty liver or liver cancer related to BCA or BCAC.

Pharmaceutical Composition

A pharmaceutical composition of the present disclosure may contain an active agent described herein and a pharmaceutically acceptable carrier. The pharmaceutically acceptable carrier is generally safe and non-toxic, and may extensively include any known substances used in the pharmaceutical industry for preparing a pharmaceutical composition, for example, a filler, a diluent, a coagulant, a binder, a lubricant, a glidant, a stabilizer, a colorant, a wetting agent, and a disintegrant. When selecting an excipient suitable for delivery of a synthetic peptide, a major concern is administration route of the pharmaceutical composition, and those skilled in the art are familiar with related knowledge. A content of the active agent in the pharmaceutical of the present disclosure can be determined according to therapeutic uses. The above pharmaceutical compositions can be prepared based on known pharmaceutical procedures recorded in detail in, for example, the book "Remington's Pharmaceutical Sciences" (Remington's Pharmaceutical Sciences, 17th Edition, edited by Alfonoso R. Gennaro, Mack Publishing Company, Easton, Pa. (1985)). The pharmaceutical of the present disclosure can take various suitable dosage forms, including but not limited to capsules, granules, tablets, pellets, oral liquids or injections.

The present disclosure will be described in detail below in connection with specific embodiments. It should be understood that these embodiments are only used to describe the present disclosure and are not intended to limit the scope of the present disclosure. The experimental methods in the following embodiments which are not specified with specific conditions are generally carried out under conventional conditions (for example, conditions disclosed in Molecular Cloning Experiment Guide, 3rd Edition, edited by J. Sambrook et al., Science Press, 2002) or conditions recommended by manufacturers.

Example 1

1. zc3h12b Gene Knockout and Identification

A CRISPR/Cas9 system was used to knock out zc3h12b gene by microinjecting a one-cell stage fertilized egg of *Oryzias latipes*. A specific method was as follows:

1) A zc3h12b gene sequence of *Oryzias latipes* (Japanese medaka HdrR) was obtained through the ensembl website (asia.ensembl.org). A target knockout site was searched for CRISPR/CAS9 editing system based on the zc3h12b gene sequence of *Oryzias latipes* on the crisprscan website (crisprscan.org). At the same time, BLAST alignment of transcriptome of *Oryzias latipes* was carried out to select candidate sites that were not predicted to have any other non-specific binding. A target site was selected at a position near the first ATG and after a promoter. A T7 promoter sequence was added before the target sequence and a gRNA scaffold sequence was added at the rear end of the target sequence. At the same time, in order to ensure efficiency of the T7 promoter, the first two bases at the 5' end of the target site were GG, if not, C was changed to G. Actual target sites of this project were as follows:

zc3h12bCrispr1:

```
                                          (SEQ ID NO: 1)
         GCATGCCACTGAGGAGTCGG
``` zc3h12bCrispr2:

```
                                          (SEQ ID NO: 2)
         GGGAGAAACTAGGCCGGTCG.
```

Synthesis was performed by Shanghai Sangon Biotech to obtain the following synthetic sequences:

(a) zc3h12bgRNA1:

```
                                                    (SEQ ID NO: 3)
5'-TAATACGACTCACTATAGGATGCCACTGAGGAGTCGGGTTTTAGAG
CTAGAAATAGC
```

(b) zc3h12bgRNA2:

```
                                                    (SEQ ID NO: 4)
5'-TAATACGACTCACTATAGGGAGAAACTAGGCCGGTCGGTTTTAGAG
CTAGAAATAGC.
```

The zc3h12bgRNA1 and zc3h12bgRNA2 were respectively subjected to PCR (94° C., 3 min, 1 round; 94° C., 30 s, 65° C. 30 s, 72° C. 1 min (34 rounds); 72° C., 5 min, 1 round), to connect to SgRNA-scaffold

```
                                                    (SEQ ID NO: 5)
5'-AAAAGCACCGACTCGGTGCCACTTTTTCAAGCTGATTACCTACTAG
AAAACTAGACCTACTAGAAA.
```

PCR products were purified by QIAquick PCR Purification Kit, and then transcribed in vitro with MAXIscript T7 In Vitro Transcription Kit (Thermo Fisher, USA) to obtain synthetic gRNAs. Mixing with Cas9 protein (GenScript Biotechnology, China) was carried out, followed by microinjection. Target knockout efficiency was detected after embryo injection, with final focus on the above two target sites.

(2) Microinjection into one-cell stage fertilized egg was carried out in two batches. Compositions of microinjection solutions were as follows:
1) gRNA1 (100 ng/µl), added with Cas9 protein (100 ng/µl);
2) gRNA1 (100 ng/µl) and gRNA2 (100 ng/µl), added with Cas9 protein (100 ng/µl).

(3) Identification of target knockout results
1) Primer synthesis

```
                                          (SEQ ID NO: 6)
Fw9: 5'-GACTTAGACGGAGAAGACCATATTAG
```

```
                                          (SEQ ID NO: 7)
Rv10: 5'-CGCACCAATTCAGCAAGAAC
```

The primers Fw9 and Rv10 can be used to specifically amplify an exon1 fragment of zc3h12b of *Oryzias latipes*, and further to distinguish a wild type from a zc3h12b knockout type.

2) DNA was extracted from fish eggs 5 days after injection to perform PCR with primers Fw9 and Rv10. PCR products were directly sequenced to determine mutation efficiencies of target sites. Compared with a normal wild type (WT), knockout embryos had obvious overlapping peaks at the target sites as shown in PCR direct sequencing results, indicating that the target sites were edited, that is, the gRNA/Cas9 system achieved an excellent editing effect.

3) Injected fish eggs were fed to adult fish, and then tail fins were cut to extract DNA. FW9 and RV10 primers were used for PCR amplification. PCR products were sequenced to confirm presence or absence of overlapping peaks to further confirm whether detected adult fish had edited zc3h12b gene. The results were shown in Table 1. A total of 134 fertilized eggs were injected in two batches of microinjection, with a survival rate of blastocysts of 76%, and a hatching rate of fry of 66%. Finally, 5 F0 brood fish were obtained (Founder: 3 single target site brood fish with 1 female and 2 male; and 2 two-target site brood fish, 1 female and 1 male, having a successful germline transmission in the offspring).

TABLE 1

Overall survival rate and germline transmission efficiency of *Oryzias latipes* with zc3h12b target gene knockout

| Group | gRNA | Number of injected fertilized egg | Blastocyst stage n, (%)[1] | Fish fry n, (%)[1] | Germline transmission Founder n, (%)[2] |
|---|---|---|---|---|---|
| 1 | gRNA1 (100 ng/µl) | 84 | 64 (76) | 55 (65) | 3-5 |
| 2 | gRNA1 (100 ng/µl) gRNA2 (100 ng/µl) | 50 | 38 (76) | 33 (66) | 2 (6) |
| Total | | 134 | 102 (76) | 88 (66) | (5) (6) |

[1] Survival percentage based on number of injected fertilized egg as denominator.
[2] Brood fish percentage based on number of fry as denominator.

2. Genetic Hybridization and Breeding of Fish of Different zc3h12b Knockout Types

*Oryzias latipes* was raised in a water circulation system at 26-28° C. with a light-dark cycle of 14/10 h, and treated in strict accordance with guidance of the Laboratory Animal Research Committee of Shanghai Ocean University. Gene-edited adult fish injected with both gRNA1 and gRNA2 target sites were used as brood fish and paired with wild-type males or females respectively. Resulted progenies were raised to adult fish, and then tail fins were cut to extract DNA. PCR was performed with FW9 and RV10 primers to identify zc3h12b genotype. PCR products were ligated into pGEM-T Easy (Promega, USA) vectors, and plasmids were extracted and sequenced to identify DNA sequences. Confirmed heterozygous male and female individuals were paired with each other. Progeny genotype identification showed that, the results were in consistent with the Mendel's law of inheritance, and finally, homozygotes with zc3h12b editing knockout were obtained.

FW9 and RV10 primers were used for specific PCR amplification of local region of exon 1 of zc3h12b in genomic DNA, to identify wild-type, heterozygous and homozygous cases. 5 types of mutations were identified: Mut 1 missing a 214 bp sequence, Mut 2 missing a 68 bp sequence, Mut 3 inserted with a 137 bp sequence, Mut 4 with 1 bp-insertion and Mut 5 with 4 bp-insertion. Based on increase or decrease of number of base of a knockout mutant, electrophoresis was used to detect and compare wild-type and knockout PCR amplification products to obtain genotypes of a wild-type and multiple mutant individuals (FIGS. 4-7).

3. Observation of Liver Entity and Histological Morphology of Wild-Type and zc3h12b Gene Knockout *Oryzias latipes*

Anatomy and physical observation of sexually mature *Oryzias latipes* (older than 3 months) were carried out. 3 male and 3 female wild-type adult fish, 2 male heterozygous fish and 5 homozygous fish were physically dissected. Tissues such as liver and gonad were routinely fixed with 4% paraformaldehyde (PFA), embed in paraffin for tissue slice (6 μm thick) (Leica RM2265 automatic microtome, Germany), and stained with hematoxylin and eosin (HE). Histological changes in, for example, livers of wild-type and zc3h12b gene knockout individuals were observed.

Figure 8:
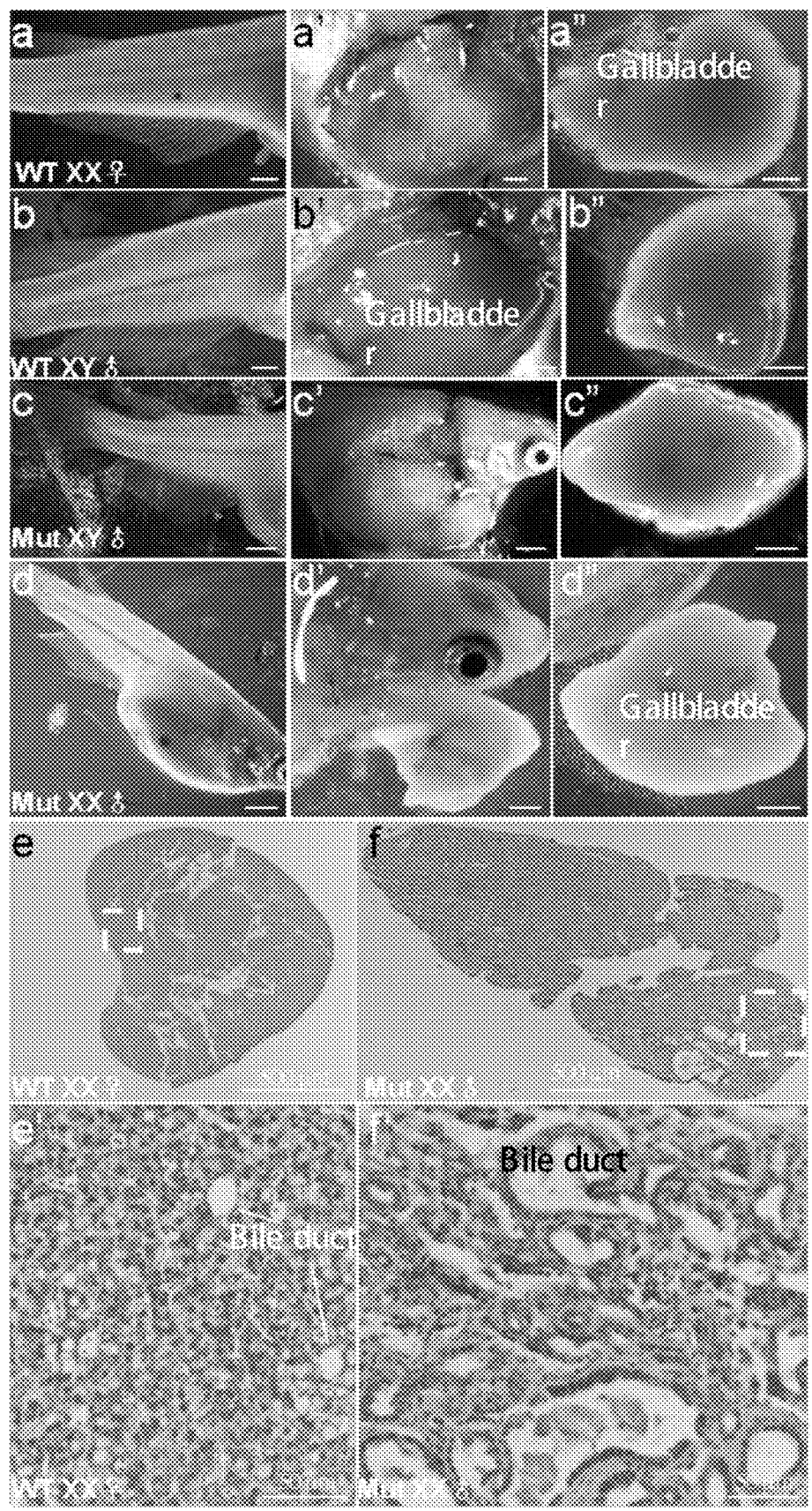
FIG. 8: morphological comparison and tissue slice analysis of livers of wild type and knockout type. Normal male and female livers a-b) are crimson or brown with soft texture. Homozygous livers of knockout type c-d) are pale yellow to milky white, with thick texture and nodules. Normal female liver slices e-e') show regularly and densely distributed hepatic sinusoids. Liver slices of knockout type f-f') have a large extent of bile duct hyperplasia and fusion as well as cholestasis, which is consistent with obvious shrinkage of gallbladder in a solid liver. e-f) show observations at low magnification while e'-f") show observations at high magnification.

Results were shown in FIG. 8. The control wild-type male and female livers were light brown (a and b in FIG. 8) while the knockout homozygous livers were slightly yellow or milky white with obvious nodules and cystic masses in the livers (c, d, c' and d' in FIG. 8). The control wild-type gallbladders were green (a" and b" in FIG. 8), while knockout homozygous gallbladders significantly shrank with cholestasis distributed in the livers (c" and d" in FIG. 8). In normal liver slices, hepatic sinusoids and hepatocytes were arranged evenly and orderly, and there was no cholestasis in bile ducts (e and e' in FIG. 8). In contrast, knockout livers had obvious cyst cavities, and at high magnification, bile duct hyperplasia, irregular fusion, cholestasis in bile ducts, hepatocyte necrosis and shedding (f and f' in FIG. 8).

4. Immunohistochemical Analysis of Antibody on Liver Cancer Surface

TABLE 2

Information of 4 antibodies used

| Antibody | Manufacturer | Immune source |
| --- | --- | --- |
| α-SMA (ab5694) | Abcam (UK) | Rabbit anti-human SMA polyclonal antibodies |
| α-CK19 (ab15463) | Abcam (UK) | Rabbit anti-human CK19 polyclonal antibodies |
| α-MMP9 (BA2202) | Boster (USA) | Rabbit anti-human MMP3 polyclonal antibodies |
| α-GPC3 (ab129381) | Abcam (UK) | Mouse anti-human GPC3 monoclonal antibody |

Rabbit anti-human α-SMA (or rabbit anti-human CK19, rabbit anti-human MMP3 and mouse anti-human GPC3 and the like) antibodies as a 1st antibody (1:100) and goat anti-rabbit (or mouse) IgG-conjugated HRP (MBL, Japan) as a secondary antibody (2nd antibody, 1:1000) were used to perform immunohistochemistry or/and immunofluorescence analysis on liver slices of the normal group and the knockout group. Color development by chemical reaction was performed with chromogenic substrate of peroxidase, diaminobenzidine (DAB, Denmark). Or, tyramide fluorescence signal amplification technology was used with TSA™ Plus Fluorescence System (PerkinElmer Life Science, USA) to observe and take images with a laser confocal microscope (Leica DMi8 TCS SP8, Germany).

Figure 9:
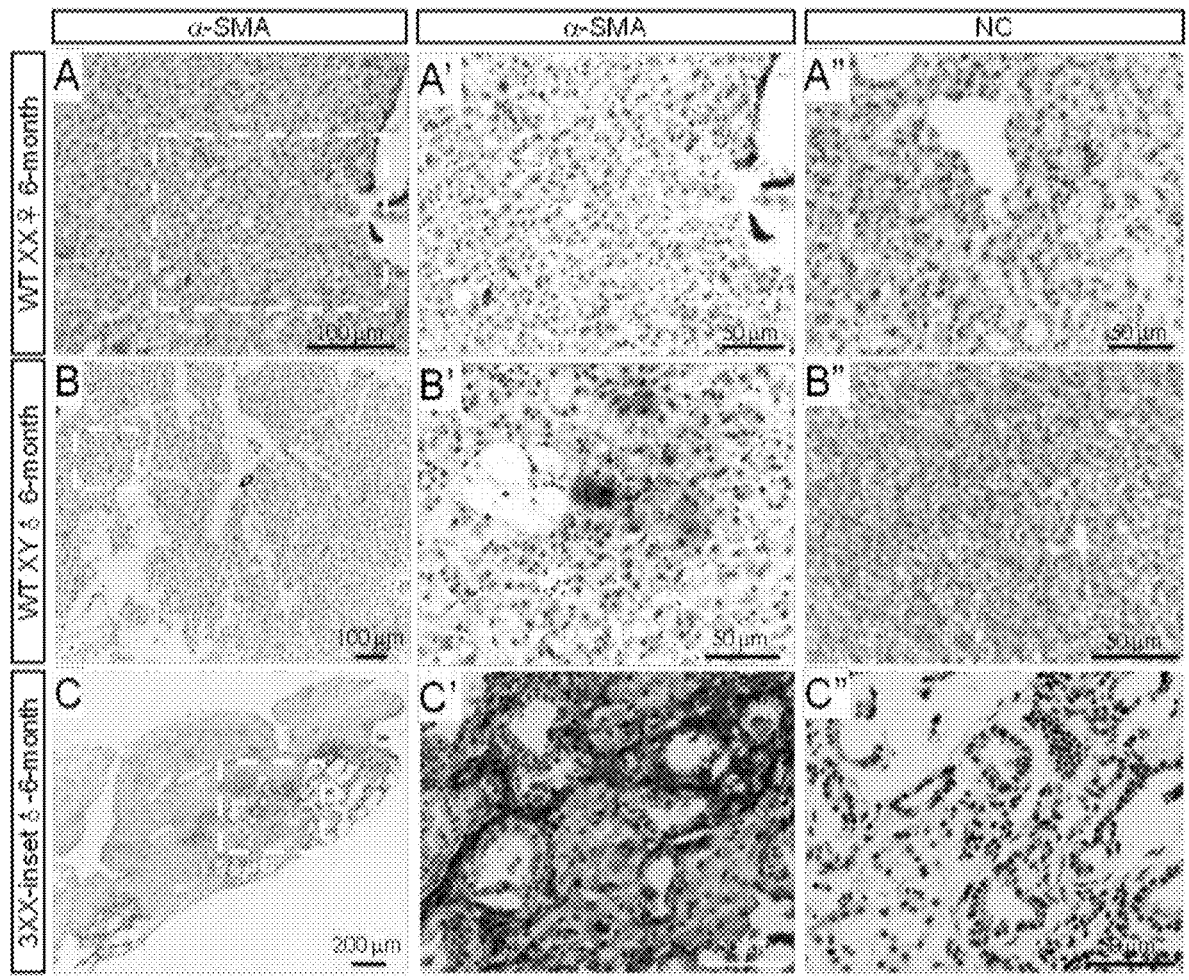
FIG. 9: Immunohistochemical analysis against human autoimmune antibody SMA. Anti-SMA immunohistochemistry results of normal female (A-A'), male (B-B') and knockout (C-C') liver slices at low and high magnifications show a large number of hyperplastic bile ducts in the knockout liver surrounded by many SMA positive cells. This is similar to the phenotype with SMA antibody positive cells surrounding a large number of hyperplastic bile ducts in a mouse liver cancer model induced by feeding with lithocholic acid (P Fickert et al., American Journal of Pathology 2006).

In wild-type 6-month-old normal liver slices, a small number of cells showed weak □-SMA positive reaction (A and A' in FIG. 9), and there were more □-SMA positive cells in cells near local fat granules in males (B and B' in FIG. 9). In knockout 6-month-old livers, there was increased abnormal proliferation of □-SMA positive cells around bile duct hyperplasia area (C and C' in FIG. 9). In negative control slices, a primary antibody was not added, so the above signals were not detected (A", B" and C" in FIG. 9), demonstrating that the signals were due to specific immune responses of the primary antibody.

Figure 10:
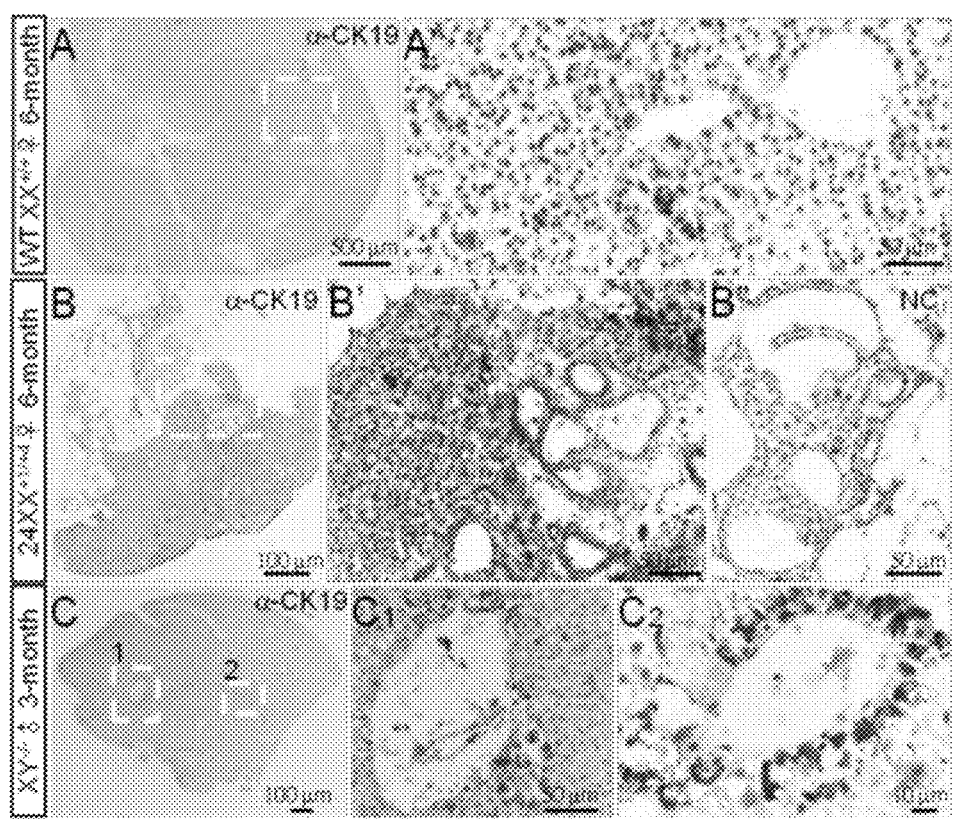
FIG. 10: Immunohistochemical analysis against human CK19. Results of immunohistochemical reactions against human CK19 of liver slices of normal females, knockout females and knockout males (low magnification: A, B, C; high magnification: A', B', C') are shown. There are only a few CK19 positive cells in normal livers, which are almost undetectable, while a large number of CK19 positive cells are present in knockout livers, gathering in hyperplastic bile ducts and tissues nearby. The negative control adds no anti-human CK19 antibody, and there is no brown signal (B" NC). This is similar to the symptoms of CK19 antibody positive cells surrounding bile duct hyperplasia in a mouse liver cancer model induced by feeding with lithocholic acid (P Fickert et al., American Journal of Pathology 2006).

CK19 was one of main antibodies for differential diagnosis of HCC and ICC. We found that, in knockout livers of males and females with an age of 3-6 months, there were different degrees of anti-human CK19 positive cells around bile ducts (FIG. 10), suggesting that the zc3h12b knockout was likely to cause cholestasis and ICC.

Figure 11:
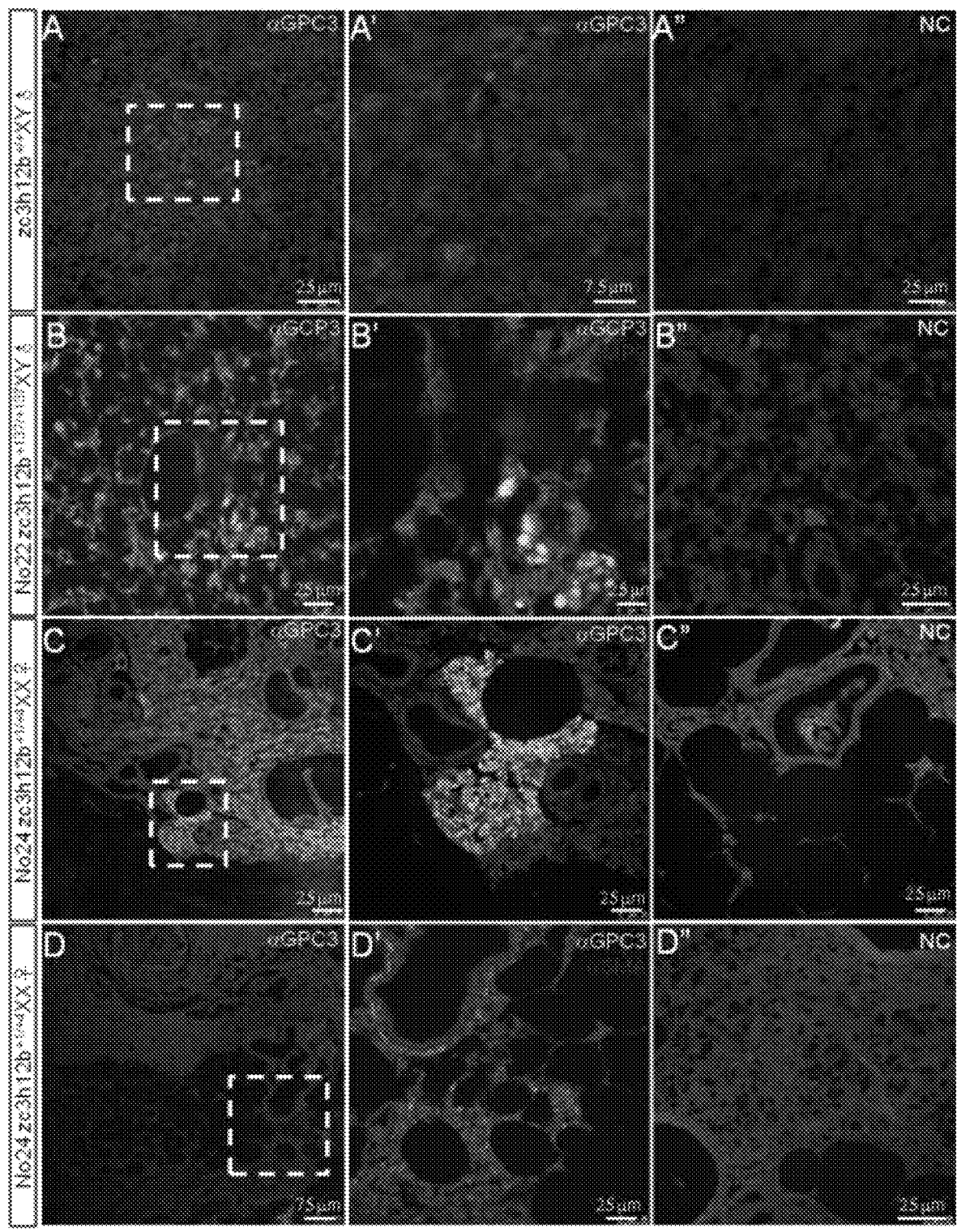
FIG. 11: Multicolor immunofluorescence reactions of liver cancer marker antibodies. Anti-GPC3 and -MMP9 reactions in the normal male liver are weak and difficult to detect. But there are a large number of anti-human GPC3, MMP9, CK19 and SMA positive cells in the zc3h12b knockout liver of *Oryzias latipes*, suggesting that these cells may have become cancerous. Anti-GPC3 (green, arrow head), anti-MMP9, anti-CK19, anti-SMA (red, arrow), nuclei are counter-stained with 4',6-diamidino-2-phenylindole (DAPI).

Both human hepatobiliary tumor cell markers, MMP9 and membranous heparan sulfate polyglycoprotein (GPC3), showed significantly higher expression in zc3h12b knockout *Oryzias latipes* liver slices compared with the normal liver control group (FIG. 11). In terms of distribution, it can be seen that, some cells expressed GPC3/MMP9 and GPC3/CK19 at the same time (B and C in FIG. 11). GPC3 and SMA were expressed in different cells (D-D' in FIG. 11, arrow referring to □-SMA positive cells, arrowheads referring to □-GPC3 positive cells).

5. Activation of a Large Amount of Macrophages with Iron Deposition in zc3h12b Knockout Livers Method for staining iron deposited macrophage with Prussian blue: a liver paraffin slice was deparaffinization with xylene routinely. Water was recovered with a series of gradient alcohol contents. Deionized water was used for rinsing for 3 times. Freshly prepared 20% hydrochloric acid+10% potassium ferrocyanide were mixed in a ratio of 1:1. Staining was carried out for 2 h at room temperature in the dark, then kept overnight at 4° C., and returned to room temperature for half an hour on the next day. Distilled water was used for washing for 3 times (5 min/time), then eosin was used for staining for 2-3 min. Dehydration was carried out with an alcohol gradient, and water was recovered in xylene. Sealing was carried out with neutral gum, and a microscope (Nikon NI-S-E) was used for observation and image taking.

Figure 12:
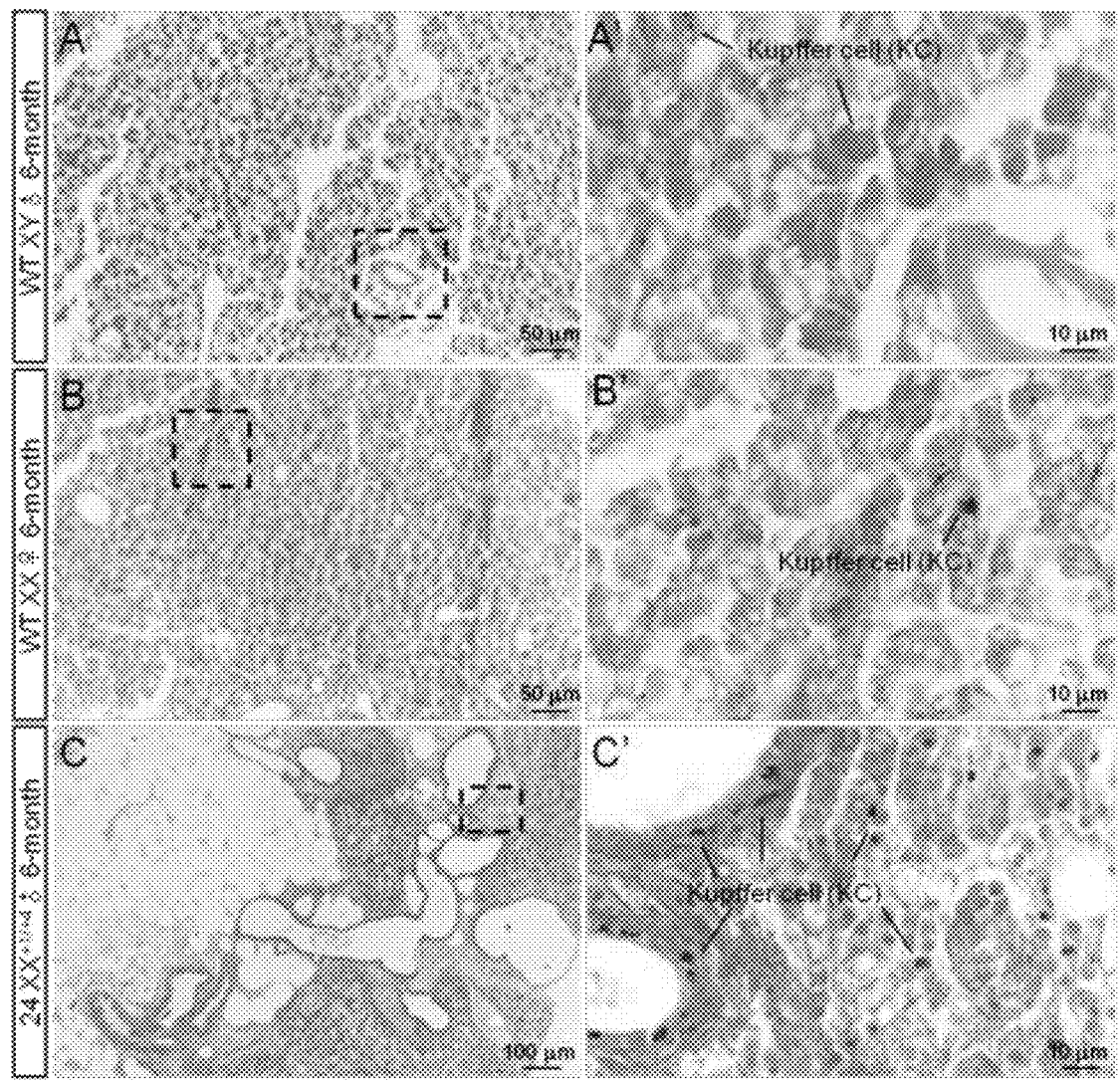
FIG. 12: Abnormal activation of macrophages in the livers of zc3h12b knockout *Oryzias latipes*. Prussian blue staining and eosin counter-staining show that, normal males (low magnification A, high magnification A') and females (low magnification B, high magnification B') have a small amount of iron-containing sinusoidal macrophages (KCs) in the liver sinusoids. These KCs abnormally proliferate in the liver of zc3h12b knockout *Oryzias latipes* (low magnification C, high magnification C').

Liver macrophages regulated and maintained local microenvironment of the liver by releasing various pro- or anti-inflammatory factors. As such, they were important natural immune cells in the liver. With iron staining by Prussian blue and counter-staining by eosin, we found a small number of Prussian blue-positive (iron-containing particles) macrophages in normal male and female livers, and activated proliferation of a large number of macrophages including iron-containing particles in zc3h12b knockout livers (FIG. 12).

In summary, by knocking out zc3h12b, the present disclosure established a fat *Oryzias latipes* which mimicked human BCA, BCAC, or fatty liver or liver cancer related to BCA or BCAC where a liver had cholestasis, bile duct hyperplasia and fusion, fatty inflammation, macrophage activation, increased human hepatobiliary tumor marker positive cells and other liver cancerous traits. The present disclosure can provide a live animal model for researches on BCA, BCAC, or fatty liver or liver cancer related to BCA or BCAC.

The above descriptions are merely preferred implementations of the present disclosure. It should be noted that a person of ordinary skill in the art may further make several improvements and modifications without departing from the methods of the present disclosure, but such improvements and modifications should be deemed as falling within the protection scope of the present disclosure.

What is claimed is:

1. A method for establishing an animal model of liver disease, comprising a step of knocking down expression of ZC3H12B gene or protein of an animal; and
   wherein the animal is selected from lower to higher vertebrates other than human.

2. The method according to claim 1, wherein the liver disease is biliary cystadenoma (BCA), biliary cystadenocarcinoma (BCAC), or fatty liver or liver cancer related to BCA or BCAC.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Target site of zc3h12b

<400> SEQUENCE: 1
gcatgccact gaggagtcgg                                              20

<210> SEQ ID NO 2
<211> LENGTH: 20
<212> TYPE: DNA
<213> ORGANISM: Artificial Sequence
<220> FEATURE:
<223> OTHER INFORMATION: Target site of zc3h12b

<400> SEQUENCE: 2
gggagaaact aggccggtcg                                              20

<210> SEQ ID NO 3
<211> LENGTH: 57
<212> TYPE: DNA
<213> ORGANISM: Artificial Sequence
<220> FEATURE:
<223> OTHER INFORMATION: An artificially synthesized primer sequence

<400> SEQUENCE: 3
taatacgact cactatagga tgccactgag gagtcgggtt ttagagctag aaatagc     57

<210> SEQ ID NO 4
<211> LENGTH: 57
<212> TYPE: DNA
<213> ORGANISM: Artificial Sequence
<220> FEATURE:
<223> OTHER INFORMATION: An artificially synthesized primer sequence

<400> SEQUENCE: 4
taatacgact cactataggg agaaactagg ccggtcggtt ttagagctag aaatagc     57

<210> SEQ ID NO 5
<211> LENGTH: 26
<212> TYPE: DNA
<213> ORGANISM: Artificial Sequence
<220> FEATURE:
<223> OTHER INFORMATION: An artificially synthesized primer sequence

<400> SEQUENCE: 5
gacttagacg gagaagacca tattag                                       26

<210> SEQ ID NO 6
<211> LENGTH: 26
<212> TYPE: DNA
<213> ORGANISM: Artificial Sequence
<220> FEATURE:
```

<223> OTHER INFORMATION: An artificially synthesized primer sequence

<400> SEQUENCE: 6
gacttagacg gagaagacca tattag                                26

<210> SEQ ID NO 7
<211> LENGTH: 20
<212> TYPE: DNA
<213> ORGANISM: Artificial Sequence
<220> FEATURE:
<223> OTHER INFORMATION: An artificially synthesized primer sequence

<400> SEQUENCE: 7
cgcaccaatt cagcaagaac                                       20

<210> SEQ ID NO 8
<211> LENGTH: 836
<212> TYPE: PRT
<213> ORGANISM: Homo sapiens

<400> SEQUENCE: 8

```
Met Thr Ala Thr Ala Glu Val Glu Thr Pro Lys Met Glu Lys Ser Ala
1               5                   10                  15

Ser Lys Glu Glu Lys Gln Gln Pro Lys Gln Asp Ser Thr Glu Gln Gly
            20                  25                  30

Asn Ala Asp Ser Glu Glu Trp Met Ser Ser Glu Ser Asp Pro Glu Gln
        35                  40                  45

Ile Ser Leu Lys Ser Ser Asp Asn Ser Lys Ser Cys Gln Pro Arg Asp
    50                  55                  60

Gly Gln Leu Lys Lys Lys Glu Met His Ser Lys Pro His Arg Gln Leu
65                  70                  75                  80

Cys Arg Ser Pro Cys Leu Asp Arg Pro Ser Phe Ser Gln Ser Ser Ile
                85                  90                  95

Leu Gln Asp Gly Lys Leu Asp Leu Glu Lys Glu Tyr Gln Ala Lys Met
            100                 105                 110

Glu Phe Ala Leu Lys Leu Gly Tyr Ala Glu Glu Gln Ile Gln Ser Val
        115                 120                 125

Leu Asn Lys Leu Gly Pro Glu Ser Leu Ile Asn Asp Val Leu Ala Glu
    130                 135                 140

Leu Val Arg Leu Gly Asn Lys Gly Asp Ser Gly Gln Ile Asn Leu
145                 150                 155                 160

Ser Leu Leu Val Pro Arg Gly Pro Ser Ser Arg Glu Ile Ala Ser Pro
                165                 170                 175

Glu Leu Ser Leu Glu Asp Glu Ile Asp Asn Ser Asp Asn Leu Arg Pro
            180                 185                 190

Val Val Ile Asp Gly Ser Asn Val Ala Met Ser His Gly Asn Lys Glu
        195                 200                 205

Glu Phe Ser Cys Arg Gly Ile Gln Leu Ala Val Asp Trp Phe Leu Asp
    210                 215                 220

Lys Gly His Lys Asp Ile Thr Val Phe Val Pro Ala Trp Arg Lys Glu
225                 230                 235                 240

Gln Ser Arg Pro Asp Ala Pro Ile Thr Asp Gln Asp Ile Leu Arg Lys
                245                 250                 255

Leu Glu Lys Glu Lys Ile Leu Val Phe Thr Pro Ser Arg Arg Val Gln
            260                 265                 270

Gly Arg Arg Val Val Cys Tyr Asp Asp Arg Phe Ile Val Lys Leu Ala
        275                 280                 285
```

```
Phe Asp Ser Asp Gly Ile Ile Val Ser Asn Asp Asn Tyr Arg Asp Leu
    290                 295                 300
Gln Val Glu Lys Pro Glu Trp Lys Lys Phe Ile Glu Glu Arg Leu Leu
305                 310                 315                 320
Met Tyr Ser Phe Val Asn Asp Lys Phe Met Pro Pro Asp Asp Pro Leu
                325                 330                 335
Gly Arg His Gly Pro Ser Leu Glu Asn Phe Leu Arg Lys Arg Pro Ile
            340                 345                 350
Val Pro Glu His Lys Lys Gln Pro Cys Pro Tyr Gly Lys Lys Cys Thr
        355                 360                 365
Tyr Gly His Lys Cys Lys Tyr Tyr His Pro Glu Arg Ala Asn Gln Pro
    370                 375                 380
Gln Arg Ser Val Ala Asp Glu Leu Arg Ile Ser Ala Lys Leu Ser Thr
385                 390                 395                 400
Val Lys Thr Met Ser Glu Gly Thr Leu Ala Lys Cys Gly Thr Gly Met
                405                 410                 415
Ser Ser Ala Lys Gly Glu Ile Thr Ser Glu Val Lys Arg Val Ala Pro
            420                 425                 430
Lys Arg Gln Ser Asp Pro Ser Ile Arg Ser Val Ala Met Glu Pro Glu
        435                 440                 445
Glu Trp Leu Ser Ile Ala Arg Lys Pro Glu Ala Ser Ser Val Pro Ser
    450                 455                 460
Leu Val Thr Ala Leu Ser Val Pro Thr Ile Pro Pro Lys Ser His
465                 470                 475                 480
Ala Val Gly Ala Leu Asn Thr Arg Ser Ala Ser Ser Pro Val Pro Gly
                485                 490                 495
Ser Ser His Phe Pro His Gln Lys Ala Ser Leu Glu His Met Ala Ser
            500                 505                 510
Met Gln Tyr Pro Pro Ile Leu Val Thr Asn Ser His Gly Thr Pro Ile
        515                 520                 525
Ser Tyr Ala Glu Gln Tyr Pro Lys Phe Glu Ser Met Gly Asp His Gly
    530                 535                 540
Tyr Tyr Ser Met Leu Gly Asp Phe Ser Lys Leu Asn Ile Asn Ser Met
545                 550                 555                 560
His Asn Arg Glu Tyr Tyr Met Ala Glu Val Asp Arg Gly Val Tyr Ala
                565                 570                 575
Arg Asn Pro Asn Leu Cys Ser Asp Ser Arg Val Ser His Thr Arg Asn
            580                 585                 590
Asp Asn Tyr Ser Ser Tyr Asn Asn Val Tyr Leu Ala Val Ala Asp Thr
        595                 600                 605
His Pro Glu Gly Asn Leu Lys Leu His Arg Ser Ala Ser Gln Asn Arg
    610                 615                 620
Leu Gln Pro Phe Pro His Gly Tyr His Glu Ala Leu Thr Arg Val Gln
625                 630                 635                 640
Ser Tyr Gly Pro Glu Asp Ser Lys Gln Gly Pro His Lys Gln Ser Val
                645                 650                 655
Pro His Leu Ala Leu His Ala Gln His Pro Ser Thr Gly Thr Arg Ser
            660                 665                 670
Ser Cys Pro Ala Asp Tyr Pro Met Pro Pro Asn Ile His Pro Gly Ala
        675                 680                 685
Thr Pro Gln Pro Gly Arg Ala Leu Val Met Thr Arg Met Asp Ser Ile
    690                 695                 700
```

-continued

```
Ser Asp Ser Arg Leu Tyr Glu Ser Asn Pro Val Gln Arg Arg Pro
705                 710                 715                 720

Pro Leu Cys Arg Glu Gln His Ala Ser Trp Asp Pro Leu Pro Cys Thr
                725                 730                 735

Thr Asp Ser Tyr Gly Tyr His Ser Tyr Pro Leu Ser Asn Ser Leu Met
                740                 745                 750

Gln Pro Cys Tyr Glu Pro Val Met Val Arg Ser Val Pro Glu Lys Met
                755                 760                 765

Glu Gln Leu Trp Arg Asn Pro Trp Val Gly Met Cys Asn Asp Ser Arg
                770                 775                 780

Glu His Met Ile Pro Glu His Gln Tyr Gln Thr Tyr Lys Asn Leu Cys
785                 790                 795                 800

Asn Ile Phe Pro Ser Asn Ile Val Leu Ala Val Met Glu Lys Asn Pro
                805                 810                 815

His Thr Ala Asp Ala Gln Gln Leu Ala Ala Leu Ile Val Ala Lys Leu
                820                 825                 830

Arg Ala Ala Arg
                835

<210> SEQ ID NO 9
<211> LENGTH: 835
<212> TYPE: PRT
<213> ORGANISM: Mus musculus

<400> SEQUENCE: 9

Met Thr Ala Thr Ala Ala Val Glu Thr Pro Lys Met Glu Lys Ser Ala
1               5                   10                  15

Ser Lys Glu Glu Lys Gln Gln Pro Lys Gln Glu Asp Ser Thr Asp Arg
                20                  25                  30

Gly Asn Ala Asp Pro Glu Glu Trp Ala Asn Ser Glu Ser Asp Pro Glu
                35                  40                  45

Gln Met Ser Cys Lys Ser Gly His Thr Ser Tyr Gln Ala Thr Asp Ile
                50                  55                  60

Gln Leu Lys Lys Lys Glu Met Pro Ser Lys Pro His Arg Pro Leu Cys
65                  70                  75                  80

Arg Ser Pro Cys Leu Asp Arg Pro Ser Phe Ser Gln Ser Ser Ile Leu
                85                  90                  95

Gln Asp Gly Lys Leu Asp Leu Glu Lys Glu Tyr Gln Ala Lys Met Asp
                100                 105                 110

Phe Ala Leu Lys Leu Gly Tyr Ala Glu Glu Gln Ile Gln Ser Val Leu
                115                 120                 125

Asn Lys Leu Gly Pro Glu Ser Leu Ile Asn Asp Val Leu Ala Glu Leu
                130                 135                 140

Val Arg Leu Gly Asn Lys Gly Asp Ser Glu Ala Gln Val Asn Leu Ser
145                 150                 155                 160

Leu Leu Leu Pro Arg Gly Ala Ser Ser Arg Glu Ile Ala Ser Pro Glu
                165                 170                 175

Leu Ser Leu Glu Asp Glu Ile Asp Asn Ser Asp Asn Leu Arg Pro Ile
                180                 185                 190

Val Ile Asp Gly Ser Asn Val Ala Met Ser His Gly Asn Lys Glu Glu
                195                 200                 205

Phe Ser Cys Arg Gly Ile Gln Leu Ala Val Asp Trp Phe Leu Asp Lys
                210                 215                 220

Gly His Lys Asp Ile Thr Val Phe Val Pro Ala Trp Arg Lys Glu Gln
225                 230                 235                 240
```

```
Ser Arg Pro Asp Ala Pro Ile Thr Asp Gln Asp Ile Leu Arg Lys Leu
            245                 250                 255

Glu Lys Glu Lys Ile Leu Val Phe Thr Pro Ser Arg Arg Val Gln Gly
            260                 265                 270

Arg Arg Val Val Cys Tyr Asp Asp Arg Phe Ile Val Lys Leu Ala Phe
            275                 280                 285

Asp Ser Asp Gly Ile Ile Val Ser Asn Asp Asn Tyr Arg Asp Leu Gln
            290                 295                 300

Val Glu Lys Pro Glu Trp Lys Lys Phe Ile Glu Glu Arg Leu Leu Met
305                 310                 315                 320

Tyr Ser Phe Val Asn Asp Lys Phe Met Pro Pro Asp Asp Pro Leu Gly
            325                 330                 335

Arg His Gly Pro Ser Leu Glu Asn Phe Leu Arg Lys Arg Pro Val Val
            340                 345                 350

Pro Glu His Lys Lys Gln Pro Cys Pro Tyr Gly Lys Lys Cys Thr Tyr
            355                 360                 365

Gly His Lys Cys Lys Tyr Tyr His Pro Glu Arg Ala Asn Gln Pro Gln
            370                 375                 380

Arg Ser Val Ala Asp Glu Leu Arg Ile Ser Ala Lys Leu Ser Thr Val
385                 390                 395                 400

Lys Ile Met Ser Glu Asp Thr Leu Ala Lys Cys Gly Ala Gly Met Ser
            405                 410                 415

Thr Ala Lys Gly Glu Ile Thr Ser Glu Ile Lys Arg Val Ala Ser Lys
            420                 425                 430

Arg Gln Ser Asp Pro Ser Ile Arg Ser Val Ala Val Glu Pro Glu Glu
            435                 440                 445

Trp Leu Ser Ile Ala Arg Lys Pro Glu Ala Ser Ser Val Pro Ser Leu
            450                 455                 460

Val Thr Ala Leu Ser Val Pro Thr Ile Pro Pro Lys Ser His Ala
465                 470                 475                 480

Val Gly Ala Leu Asn Thr Arg Ser Ala Ser Ser Pro Val Pro Gly Ser
            485                 490                 495

Ser His Phe Pro His Gln Lys Ala Ser Leu Glu His Met Val Ser Met
            500                 505                 510

Gln Tyr Pro Pro Ile Leu Val Thr Asn Ser His Gly Thr Pro Ile Asn
            515                 520                 525

Tyr Thr Glu Gln Tyr Pro Lys Phe Glu Thr Met Gly Asp His Asp Tyr
            530                 535                 540

Tyr Ser Val Leu Ser Asp Phe Ser Lys Leu Ser Ile Asn Asn Met His
545                 550                 555                 560

Asn His Glu Tyr Tyr Met Ala Glu Ala Asn Gln Gly Val Tyr Val Arg
            565                 570                 575

Asn Pro Gly Leu Cys Thr Asp Ser His Met Ser His Thr Arg Asn Asp
            580                 585                 590

Asn Tyr Ser Ser Tyr Asn Asn Leu Tyr Leu Ala Val Ala Asp Ala His
            595                 600                 605

Pro Glu Gly Thr Leu Lys Leu His Arg Ser Ala Ser His Asn His Leu
            610                 615                 620

Gln Pro Phe Ser His Gly Tyr His Glu Ala Leu Ala Arg Val Gln Ser
625                 630                 635                 640

Tyr Gly Ser Glu Asp Ser Lys Gln Ala Pro His Lys Gln Ser Val Pro
            645                 650                 655
```

```
His Leu Ala Val His Thr Gln Asn Pro Ala Thr Gly Ala His Ser Ser
                660                 665                 670

Cys Pro Gly Asp Tyr Thr Met Pro Pro Ser Ile His Pro Val Gly Pro
            675                 680                 685

Ser Gln Pro Gly Arg Ala Leu Val Met Thr Arg Met Asp Ser Ile Ser
        690                 695                 700

Asp Ser Arg Leu Tyr Asp Ser Asn Pro Met Arg Gln Arg Arg Pro Pro
705                 710                 715                 720

Leu Cys Arg Glu Gln His Ala Ser Trp Asp Pro Leu Pro Cys Thr Ala
                725                 730                 735

Asp Ser Tyr Gly Tyr His Ser Tyr Pro Leu Gly Asn Ser Leu Met Gln
            740                 745                 750

Pro Cys Tyr Glu Pro Val Met Val Arg Ser Met Pro Glu Lys Met Glu
        755                 760                 765

Gln Leu Trp Arg Asn Pro Trp Val Gly Met Cys Asn Asp Ser Arg Glu
    770                 775                 780

His Met Ile Pro Glu His Gln Tyr Gln Thr Tyr Lys Asn Leu Cys Asn
785                 790                 795                 800

Ile Phe Pro Ser Asn Ile Val Leu Ala Val Met Glu Lys Asn Pro His
                805                 810                 815

Thr Ala Asp Ala Gln Gln Leu Ala Ala Leu Ile Val Ala Lys Leu Arg
            820                 825                 830

Ala Ala Arg
        835

<210> SEQ ID NO 10
<211> LENGTH: 837
<212> TYPE: PRT
<213> ORGANISM: Gallus gallus

<400> SEQUENCE: 10

Met Thr Ala Trp Ser Met Val Gly Lys Leu Lys Met Glu Lys Arg His
1               5                   10                  15

Ser Arg Glu Asp Arg Asn Val Glu Gln Asp Ala Gly Glu Cys Ser Ala
            20                  25                  30

Glu Ser Glu Glu Trp Thr Ser Ser Ser Glu Pro Glu Gln Pro Tyr
        35                  40                  45

Phe Arg Ser Ser Cys Ser Asn Ile Pro Trp Arg Glu Lys Glu Val Pro
    50                  55                  60

Pro Lys Pro His Arg Pro Leu Cys Arg Ser Pro Cys Leu Asp Arg Pro
65                  70                  75                  80

Ser Phe Ser Gln Ser Ser Ile Thr Gln Asp Leu Lys Leu Glu Glu Cys
                85                  90                  95

Lys Thr Asn Leu Asp Lys Glu Tyr Gln Ala Lys Met Asp Phe Ala Leu
            100                 105                 110

Lys Leu Gly Tyr Ala Gly Asp Gln Ile Gln Ala Val Leu Asn Lys Leu
        115                 120                 125

Gly Ala Asp Ala Leu Ile Asn Asp Val Leu Ala Glu Leu Val Arg Leu
    130                 135                 140

Gly Asn Lys Ser Glu Ser Glu Gly Gln Asn Ser Ala Ser Ser Thr Thr
145                 150                 155                 160

Ser Thr Leu Val Pro Arg Gly Pro Cys Pro Lys Glu Ile Ala Ser Pro
                165                 170                 175

Glu Leu Ser Leu Glu Asp Glu Val Val Asp Asn Ser Asp Asn Leu Arg
            180                 185                 190
```

```
Pro Ile Val Ile Asp Gly Ser Asn Val Ala Met Ser His Gly Asn Lys
    195                 200                 205

Glu Gly Phe Ser Cys Arg Gly Ile Gln Leu Ala Val Asp Trp Phe Leu
210                 215                 220

Glu Lys Gly His Lys Asp Ile Thr Val Phe Val Pro Ala Trp Arg Lys
225                 230                 235                 240

Glu Gln Ser Arg Pro Asp Ala Pro Ile Thr Asp Gln Glu Ile Leu Arg
                245                 250                 255

Lys Leu Glu Lys Glu Lys Ile Leu Val Phe Thr Pro Ser Arg Arg Val
            260                 265                 270

Gln Gly Arg Arg Val Val Cys Tyr Asp Asp Arg Phe Ile Val Lys Leu
        275                 280                 285

Ala Phe Asp Ser Asp Gly Ile Ile Val Ser Asn Asp Asn Tyr Arg Asp
    290                 295                 300

Leu Gln Asn Glu Lys Pro Glu Trp Lys Lys Phe Ile Glu Glu Arg Leu
305                 310                 315                 320

Leu Met Tyr Ser Phe Val Asn Asp Lys Phe Met Pro Pro Asp Asp Pro
                325                 330                 335

Leu Gly Arg His Gly Pro Ser Leu Glu Asn Phe Leu Arg Lys Arg Pro
            340                 345                 350

Val Ile Pro Glu His Lys Lys Gln Pro Cys Pro Tyr Gly Lys Lys Cys
        355                 360                 365

Thr Tyr Gly His Lys Cys Lys Tyr Tyr His Pro Glu Arg Ala Asn Gln
    370                 375                 380

Pro Gln Arg Ser Val Ala Asp Glu Leu Arg Ile Ser Ala Lys Leu Ser
385                 390                 395                 400

Ala Val Lys Thr Met Ser Glu Gly Ala Leu Ala Lys Cys Gly Thr Gly
                405                 410                 415

Pro Ser Ser Ser Lys Gly Glu Ile Ser Ser Glu Val Lys Arg Ile Ala
            420                 425                 430

Pro Lys Arg Gln Ser Asp Pro Ser Ile Arg Ser Val Ala Val Glu Pro
        435                 440                 445

Glu Glu Lys Leu Thr Val Ala Arg Lys Ser Glu Ala Asn Ser Val Pro
    450                 455                 460

Ser Leu Val Ser Ala Leu Ser Val Pro Thr Leu Pro Pro Lys Ser
465                 470                 475                 480

His Ala Ala Gly Ala Leu Asn Thr Arg Ser Ala Ser Ser Pro Val Pro
                485                 490                 495

Gly Ser Ser Gln Phe Thr His Gln Lys Ser Ser Leu Glu His Met Ser
            500                 505                 510

Ser Val Gln Tyr Pro Pro Ile Leu Val Thr Asn Ser His Gly Thr Ser
        515                 520                 525

Ile Ser Tyr Thr Asp Gln Tyr Pro Lys Tyr Glu Ser Leu Gly Asp His
    530                 535                 540

Gly Tyr Tyr Ser Leu Leu Ser Asp Phe Ser Asn Leu Ser Ile Ser Ser
545                 550                 555                 560

Met His Asn Thr Asp Tyr Tyr Gly Ala Asp Met Asp Gln Gly Met Tyr
                565                 570                 575

Ser Arg Asn Ser Ser Pro Cys Pro Asp Asn Cys Leu Ser His Thr Asn
            580                 585                 590

Asn Asp Ser Tyr Ser Ser Tyr Asn Asp Leu Tyr Leu Gly Val Ala Asp
        595                 600                 605
```

```
Ala Ser Pro Glu Asp Asn Val Lys Ile His Arg Leu Thr Ser Gln Asn
            610                 615                 620

Arg Leu Gln Pro Phe Pro His Gly Tyr His Glu Ala Leu Asn Arg Val
625                 630                 635                 640

Gln Ser Phe Gly Thr Glu Glu Pro Gln Gln Ser Leu Arg Lys Gln Ser
            645                 650                 655

Val Ser His Leu Gly Leu His Ala Gln His Pro Val Val Gly Ala Arg
            660                 665                 670

Ser Ser Cys Pro Gly Glu Tyr Pro Val Pro Gln Asn Ile His Pro Ser
            675                 680                 685

Thr Ala Gln Pro Ser Arg Ala Leu Val Met Thr Arg Met Asp Ser Ile
            690                 695                 700

Ser Asp Ser Arg Leu Tyr Glu Ser Asn Pro Thr Arg Gln Arg Arg Pro
705                 710                 715                 720

Pro Leu Cys Arg Glu Gln His Ala Ser Trp Asp Pro Leu Pro Cys Ala
            725                 730                 735

Ser Asp Ser Tyr Thr Tyr His Ser Tyr Pro Leu Ser Asn Asn Leu Met
            740                 745                 750

Gln Pro Cys Tyr Glu Pro Val Met Val Arg Ser Met Pro Glu Lys Met
            755                 760                 765

Glu Gln Leu Trp Arg Asn Pro Trp Ile Gly Ile Cys Gly Glu Pro Arg
770                 775                 780

Glu Pro His Ile Ile Pro Glu His Gln Tyr Gln Thr Tyr Lys Asn Leu
785                 790                 795                 800

Cys Asn Ile Phe Pro Pro Ser Ile Val Leu Ser Val Met Glu Lys Asn
            805                 810                 815

Pro His Met Thr Asp Ala Gln Gln Leu Ala Ala Met Ile Val Ala Lys
            820                 825                 830

Leu Arg Thr Gly Arg
            835

<210> SEQ ID NO 11
<211> LENGTH: 845
<212> TYPE: PRT
<213> ORGANISM: Oryzias latipes

<400> SEQUENCE: 11

Met Thr Ala Trp Ser Thr Val Glu Lys Leu Lys Met Glu Lys Arg Pro
1               5                   10                  15

Cys Arg Glu Glu Asn Ile Asp Ser Ser Glu Ala Gln His Ala Thr Glu
            20                  25                  30

Glu Ser Glu Asp Gly Ser Ser Ser Glu Ser Glu Ser Glu Glu Gln Lys
            35                  40                  45

Pro Gln Arg Val Gln Ala Asn Ser Ser Ser Cys Lys Arg Glu Pro
50                  55                  60

Leu Ala Val Thr Lys Pro His Arg Gln Leu Cys Arg Ser Pro Cys Leu
65                  70                  75                  80

Asp Arg Pro Ser Phe Ser Gln Ser Ser Thr Val Gln Asp Phe Arg Glu
            85                  90                  95

Asp Asp Thr Ser Thr Ala Ser Gly Val Lys Pro Val Ser Glu Arg Glu
            100                 105                 110

Tyr Gln Thr Lys Ile Glu Phe Ala Leu Lys Leu Gly Tyr Ser Gly Glu
            115                 120                 125

Gln Val Glu Ser Val Leu Ser Lys Leu Gly Ala Ala Ala Leu Ile Asn
130                 135                 140
```

```
Asp Val Leu Ala Glu Leu Val Arg Leu Gly Asn Lys Val Glu Pro Glu
145                 150                 155                 160

Thr Gln Pro Cys Ser Thr Ala Ala Pro Val Ser Trp Pro Pro Cys
            165                 170                 175

Val Lys Glu Thr Val Ser Pro Glu Val Ser Val Glu Gly Asp Ser Val
            180                 185                 190

Asp Thr Tyr Asp Asn Leu Arg Pro Ile Val Ile Asp Gly Ser Asn Val
            195                 200                 205

Ala Met Ser His Gly Asn Lys Glu Val Phe Ser Cys Arg Gly Ile Gln
            210                 215                 220

Leu Ala Val Glu Trp Phe Arg Asp Lys Gly His Lys Asp Ile Thr Val
225                 230                 235                 240

Phe Val Pro Ala Trp Arg Lys Glu Gln Ser Arg Pro Asp Ser Leu Ile
                245                 250                 255

Thr Asp Gln Glu Ile Leu Arg Lys Leu Glu Lys Glu Lys Ile Leu Val
                260                 265                 270

Phe Thr Pro Ser Arg Arg Val Gln Gly Arg Arg Val Val Cys Tyr Asp
                275                 280                 285

Asp Arg Phe Ile Val Lys Leu Ala Tyr Asp Ser Asp Gly Ile Ile Val
    290                 295                 300

Ser Asn Asp Asn Tyr Arg Asp Leu Gln Asn Glu Lys Pro Glu Trp Lys
305                 310                 315                 320

Lys Phe Ile Glu Glu Arg Leu Leu Met Tyr Ser Phe Val Asn Asp Lys
                325                 330                 335

Phe Met Pro Pro Asp Asp Pro Leu Gly Arg His Gly Pro Ser Leu Glu
                340                 345                 350

Asn Phe Leu Arg Lys Arg Pro Val Val Pro Glu His Lys Lys Gln Pro
                355                 360                 365

Cys Pro Tyr Gly Lys Lys Cys Thr Tyr Gly His Lys Cys Lys Tyr Tyr
    370                 375                 380

His Pro Glu Arg Val Asn Gln Pro Leu Arg Ser Val Ala Asp Glu Leu
385                 390                 395                 400

Arg Ala Phe Ala Lys Leu Ser Ala Val Lys Thr Met Ser Glu Gly Ala
                405                 410                 415

Leu Val Lys Cys Gly Thr Gly Ala Ala Thr Val Lys Gly Asp Ser Ser
                420                 425                 430

Ser Glu Ala Lys Arg Val Ala Pro Lys Arg Gln Ser Asp Pro Ser Ile
            435                 440                 445

Arg Ser Val Ala Cys Glu Pro Pro Glu Ala Leu Ser Ile Val Arg Lys
    450                 455                 460

Ser Glu Thr Asn Ser Val Pro Ser Leu Val Ser Ala Leu Ser Val Pro
465                 470                 475                 480

Thr Met Gln Pro Ala Lys Ser His Ala Ala Gly Ala Leu Asn Thr Arg
                485                 490                 495

Ser Ala Ser Ser Pro Val Pro Gly Ser Leu Gln Phe Ser His Ser Ser
            500                 505                 510

Leu Glu His Met Ser Ser Val Gln Tyr Pro Pro Ile Leu Val Thr Asn
            515                 520                 525

Ser His Gly Ala Ser Ile Thr Tyr Ser Glu Pro Phe Pro Lys Tyr Asp
    530                 535                 540

Ser Val Ser Asp His Gly Tyr Tyr Ser Leu His Ser Asp Phe Ser Asn
545                 550                 555                 560
```

-continued

```
Met Ser Met Ser Ser Met His Asn Val Asp Ser Phe Cys Ser Met Glu
            565             570             575
His Glu His Val Tyr Gln Arg Asn Pro Ser His Cys Pro Glu Ser Cys
            580             585             590
Leu Ser His Ser Asn Ser Asp Ser Phe Ser Ser Tyr Gly Asp Met Tyr
            595             600             605
Pro Ser Ser Met Asp Ser Ser Leu Glu Glu Ser Met Lys Gly Ser Gln
            610             615             620
Gln Ala Pro Ala Gln Ala Arg Met Gln Ala Phe Ser His Gly Phe Arg
625             630             635             640
His Glu Ala Leu Thr Arg Val Gln Ser Tyr Gly Pro Glu Glu Pro Lys
            645             650             655
Gln Cys Ser Arg Lys Gln Ser Gly Ala His Leu Ala Pro His Ile Gln
            660             665             670
His Ala Ala Val Gly Ala Arg Ser Ser Cys Pro Gly Asp Tyr Pro Leu
            675             680             685
Thr Gln Asn Cys Leu Pro Pro Leu Ser Ser Gln Pro Thr Arg Ser Leu
            690             695             700
Gly Met Thr Arg Met Asp Ser Ile Ser Asp Ser Arg Leu Tyr Asp Ser
705             710             715             720
Asn Pro Met Arg Gln Arg Arg Pro Pro Leu Cys Arg Glu Gln His Ala
            725             730             735
Ser Trp Asp Pro Leu Pro Cys Gly Asn Glu Ser Phe Gly Tyr His Ser
            740             745             750
Tyr Pro Leu Ser Asn Ser Leu Met Pro Cys Cys Glu Arg Val Met Val
            755             760             765
Arg Ser Met Pro Asp Lys Met Glu Gln Ile Trp Ser Ser Pro Trp Glu
            770             775             780
Thr Pro Ser Ala Ala Glu His Gln Glu Gln His Ala Val Pro Asp His
785             790             795             800
Gln Tyr Gln Thr Tyr Arg Asn Leu Cys Asn Ile Phe Pro Ala Tyr Ile
            805             810             815
Val His Ala Val Met Glu Lys Asn Pro His Leu Thr Asp Pro Gln Gln
            820             825             830
Leu Ala Ala Val Ile Val Thr Lys Leu Arg Ser Asn His
            835             840             845
```